(12) United States Patent
Yedgar

(10) Patent No.: US 8,372,815 B2
(45) Date of Patent: *Feb. 12, 2013

(54) USE OF LIPID CONJUGATES IN THE TREATMENT OF CONJUNCTIVITIS

(75) Inventor: Saul Yedgar, Jerusalem (IL)

(73) Assignee: Yissum Research Development Company, Jerusalem (IL)

( * ) Notice: Subject to any disclaimer, the term of this patent is extended or adjusted under 35 U.S.C. 154(b) by 229 days.

This patent is subject to a terminal disclaimer.

(21) Appl. No.: 12/605,887

(22) Filed: Oct. 26, 2009

(65) Prior Publication Data

US 2010/0087397 A1    Apr. 8, 2010

Related U.S. Application Data

(63) Continuation of application No. 11/475,240, filed on Jun. 27, 2006, now Pat. No. 7,608,598, which is a continuation-in-part of application No. 10/952,496, filed on Sep. 29, 2004, now Pat. No. 7,393,938, which is a continuation-in-part of application No.

(Continued)

(51) Int. Cl.
    *A61K 31/70* (2006.01)
(52) U.S. Cl. .................................... 514/42
(58) Field of Classification Search ............ 514/42
    See application file for complete search history.

(56) References Cited

U.S. PATENT DOCUMENTS

| | | | |
|---|---|---|---|
| 4,604,376 A | 8/1986 | Teng | |
| 4,624,919 A | 11/1986 | Kokusho et al. | |
| 4,654,327 A | 3/1987 | Teng | |
| 5,064,817 A | 11/1991 | Yedgar et al. | |
| 5,169,636 A | 12/1992 | Nanba et al. | |
| 5,354,853 A | 10/1994 | Staveski et al. | |
| 5,401,511 A | 3/1995 | Margalit | |
| 5,401,777 A | 3/1995 | Ammon et al. | |
| 5,464,942 A | 11/1995 | Sakurai et al. | |
| 5,470,578 A | 11/1995 | Aoki et al. | |
| 5,512,671 A | 4/1996 | Piantadosi et al. | |
| 5,587,363 A | 12/1996 | Henderson | |
| 5,707,821 A | 1/1998 | Rydel et al. | |
| 5,733,892 A | 3/1998 | Sakurai et al. | |
| 5,785,975 A | 7/1998 | Parikh | |
| 6,022,866 A | 2/2000 | Falk et al. | |
| 6,043,231 A | 3/2000 | Pruzanski et al. | |
| 6,071,532 A | 6/2000 | Chaikof et al. | |
| 6,162,787 A | 12/2000 | Sorgente et al. | |
| 6,171,614 B1 | 1/2001 | Chaikof et al. | |
| 6,180,596 B1 | 1/2001 | Tsao | |
| 6,325,385 B1 | 12/2001 | Iwashita et al. | |
| 6,749,813 B1 | 6/2004 | David et al. | |
| 7,034,006 B2 | 4/2006 | Yedgar et al. | |
| 7,101,859 B2 | 9/2006 | Yedgar et al. | |
| 7,141,552 B2 | 11/2006 | Yedgar et al. | |
| 7,393,938 B2 | 7/2008 | Yedgar | |
| 7,504,384 B2 * | 3/2009 | Yedgar et al. | 514/42 |
| 7,608,598 B2 * | 10/2009 | Yedgar | 514/42 |

FOREIGN PATENT DOCUMENTS

| | | |
|---|---|---|
| EP | 0236951 | 9/1987 |
| EP | 0529659 | 3/1993 |
| EP | 0581281 | 2/1994 |
| EP | 0581282 B | 2/1994 |
| EP | 1046394 | 10/2000 |
| JP | 04082893 | 3/1992 |
| JP | 09030979 | 2/1997 |
| JP | 2002345455 | 12/2002 |
| JP | 2003160498 | 3/2003 |
| JP | 2003335801 | 11/2003 |
| JP | 2004018841 | 1/2004 |
| JP | 2004170194 | 6/2004 |
| WO | WO 87/02777 | 5/1987 |
| WO | WO 91/00289 | 1/1991 |
| WO | WO 96/04001 | 2/1996 |
| WO | WO 96/11670 | 4/1996 |
| WO | WO 96/28544 | 9/1996 |
| WO | WO 97/01330 | 1/1997 |
| WO | WO 97/48337 | 12/1997 |
| WO | WO 98/16198 | 4/1998 |
| WO | WO 98/51285 | 11/1998 |
| WO | WO 01/51003 | 7/2001 |
| WO | WO 01/91805 | 12/2001 |
| WO | WO 2005/084307 | 9/2005 |

OTHER PUBLICATIONS

Ehehalt, R. et al., "Lipid Based Therapy for Ulcerative Colitis—Modulation of Intestinal Mucus Membrane Phospholipids as a Tool to Influence Inflammation," Int. J. Mol. Sci. 2010, 11, 4149-4164.

Phyllis, Dan et al., "Inhibition of Type I and Type II Phospholipase A2 by Phosphatidyl-Ethanolamine Linked to Polymeric Carriers," Biochemistry, 1998, 37 (17), pp. 6199-6204.

Extended European Search Report of European Application No. 05808267.8 issued Mar. 15, 2012.

Cummings, B.S., "Phospholipase $A_2$ as targets for anti-cancer drugs," Biochemical Pharmacology 74 (2007), pp. 949-959.

Kokotos, G. et al., "Novel 2-Oxoamide Inhibitors of Human Group IVA Phospholipase $A_2$," J. Med. Chem., 2002, 45, pp. 2891-2893.

Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" Cancer Res 47(12):3239-45.

Balsinde, J, Balboa, MA, Yedgar, S and Dennis, EA (2000) "Group V phospholipase A(2)-mediated oleic acid mobilization in lipopolysaccharide-stimulated P388D(1) macrophages" J Biol Chem 275(7):4783-6.

Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" Br J Pharmacol 135(7):1665-74.

Brenner, T, Arnon, R, Sela, M, Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" J Neuroimmunol 115(1-2):152-60.

(Continued)

Primary Examiner — Rei-tsang Shiao

(74) Attorney, Agent, or Firm — Mark S. Cohen; Pearl Cohen Zedek Latzer, LLP

(57) ABSTRACT

In one embodiment, the invention provides a method of suppressing, inhibiting, preventing, or treating conjunctivitis in a subject, comprising the step of administering an effective amount of a lipid or phospholipid moiety bound via an ester or amide bond to a physiologically acceptable monomer, dimer, oligomer, or polymer, and/or a pharmaceutically acceptable salt or a pharmaceutical product thereof to a subject with conjunctivitis.

20 Claims, 12 Drawing Sheets

Related U.S. Application Data

09/756,765, filed on Jan. 10, 2001, now Pat. No. 7,034,006.

(60) Provisional application No. 60/174,905, filed on Jan. 10, 2000, provisional application No. 60/174,907, filed on Jan. 10, 2000.

(56) References Cited

OTHER PUBLICATIONS

Brenner, T, Lisak, RP, Rostami, A, Pleasure, DE and Silberberg, DH (1986) "Astrocytes, oligodendrocytes, and Schwann cells share a common antigenic determinant that cross-reacts with myelin basic protein identification with monoclonal antibody" *J Neurosci* 6(7):1925-33.

Brenner, T, Poradosu, E, Soffer, D, Sicsic, C, Gazit, A and Levitzki, A (1998) "Suppression of experimental autoimmune encephalomyelitis by tyrphostin AG-556" *Exp Neurol* 154(2):489-98.

Cabanas, C and Hogg, N (1993) "Ligand intercellular adhesion molecule 1 has a necessary role in activation of integrin lymphocyte function-associated molecule 1" *Proc Natl Acad Sci U S A* 90(12) 5838-42.

Chen, WM, Soria, J, Soria, C, Krimsky, M and Yedgar, S (2002) "Control of capillary formation by membrane-anchored extracellular inhibitor of phospholipase A(2)" *FEBS Lett* 522(1-3):113-8.

Dan, P, Dagan, A, Krimsky, M, Pruzanski, W, Vadas, P and Yedgar, S (1998) "Inhibition of type I and type II phospholipase A2 by phosphatidyl-ethanolamine linked to polymeric carriers" *Biochemistry* 37(17):6199-204.

Darville, T, Yedgar, S, Krimsky, M, Andrews, CW, Jr., Jungas, T and Ojcius, DM (2004) "Protection against Chlamydia trachomatis infection in vitro and modulation of inflammatory response in vivo by membrane-bound glycosaminoglycans" *Microbes Infect* 6(4):369-76.

Davidson, FF, Dennis, EA, Powell, M and Glenney, Jr, Jr. (1987) "Inhibition of phospholipase A2 by "lipocortins" and calpactins. An effect of binding to substrate phospholipids" *J Biol Chem* 262(4):1698-705.

Greaves MW and Camp RD (1988) "Prostaglandins, leukotrienes, phospholipase, platelet activating factor, and cytokines: an integrated approach to inflammation of human skin." *Arch Dermatol Res* 280 S33-41.

Krimsky, M, Dagan, A, Aptekar, L, Ligumsky, M and Yedgar, S (2000) "Assessment of intestinal permeability in rats by permeation of inulin-fluorescein" *J Basic Clin Physiol Pharmacol* 11(2):143-53.

Krimsky, M, Yedgar, S, Aptekar, L, Schwob, O, Goshen, G, Gruzman, A, Sasson, S and Ligumsky, M (2003) "Amelioration of TNBS-induced colon inflammation in rats by phospholipase A2 inhibitor" *Am J Physiol Gastrointest Liver Physiol* 285(3):G586-92.

Margolis-Nunno, H, Ben-Hur, E, Gottlieb, P, Robinson, R, Oetjen, J and Horowitz, B (1996) "Inactivation by phthalocyanine photosensitization of multiple forms of human immunodeficiency virus in red cell concentrates" *Transfusion* 36(8):743-50.

Murthy, SN, Cooper, HS, Shim, H, Shah, RS, Ibrahim, SA and Sedergran, DJ (1993) "Treatment of dextran sulfate sodium-induced murine colitis by intracolonic cyclosporin" *Dig Dis Sci* 38(9):1722-34.

Okayasu, I, Hatakeyama, S, Yamada, M, Ohkusa, T, Inagaki, Y and Nakaya, R (1990) "A novel method in the induction of reliable experimental acute and chronic ulcerative colitis in mice" *Gastroenterology* 98(3):694-702.

Schmiel, DH and Miller, VL (1999) "Bacterial phospholipases and pathogenesis" *Microbes Infect* 1(13):1103-12.

Schnitzer, E, Dagan, A, Krimsky, M, Lichtenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" *Chem Phys Lipids* 104(2):149-60.

Schnitzer, E, Yedgar, S, Danino, D, Talmon, Y and Lichtenberg, D (1999) "The Interaction of hyaluronic-phosphatidylethanolamine with low density lipoprotein (LDL) and its effect on copper induced LDL oxidation" *Biophysical Journal* 76(1): Part 2.

Schnitzer, E, Pinchuk, I, Fainaru, M, Lichtenberg, D and Yedgar, S (1998) "LDL-associated phospholipase A does not protect LDL against lipid peroxidation in vitro" *Free Radic Biol Med* 24(7-8):1294-303.

Wang D.P, Matthias Schuster, Yi Fong Wang, Chi Huey Wong "Synthesis of Phospholipid-Inhibitor Conjugates by Enzymic Transphosphatidylation With Phospholipase", J. Am Chem. Soc.; 1993; 115(23); 10487-10491.

Carey et al, "Contrasting Effects of Cycloxygenase-1 (COX-1) and COX-2 Deficiency in the Host Response to Influenze, A Viral Infection". Journ. of Immunology 2005, vol. 15: 175 (10): 6878-84.

Teitelbaum D, Arnon R, Sela M, Rabinsohn Y, Shapiro D., "Sphingomyelin Specific Antibodies Elicited by Synthetic Conjugates," Immunochemistry. Nov. 1973;10(11):735-43.

Weltzien Hu, Matthiessen HP, Meyer-Delius M, Zimmermann F, Rüde E., "Acidic "Peptidophospholipids", A New Class of Hapten-Bearing Cell Surface Modifying Reagents," Mol Immunol. Sep. 1984;21(9);801-10.

Winger TM, Ludovice PJ, Chaikof EL, "Lipopeptide Conjugates Biomolecular Building Blocks for Receptor Activating Membrane-Mimetic Structures," Biomaterials. Feb. 1996;17(4):437-41.

Office Action of U.S. Appl. No. 11/220,965 Dated Mar. 27, 2008.
Office Action of U.S. Appl. No. 11/598,812 Dated Dec. 19, 2008.
Office Action of U.S. Appl. No. 10/989,606 Dated Sep. 1, 2009.
Supplementary Search Report of European Application No. 05724186.1 Dated Nov. 17, 2009.
Office Action of Japanese Application No. 2001-551427 Dated Nov. 20, 2009.

\* cited by examiner

Fig. 1: Effect of Compound XXVI on allergic conjunctivitis in guinea pigs. Corneal opacities at the immediate post-provocation phase.
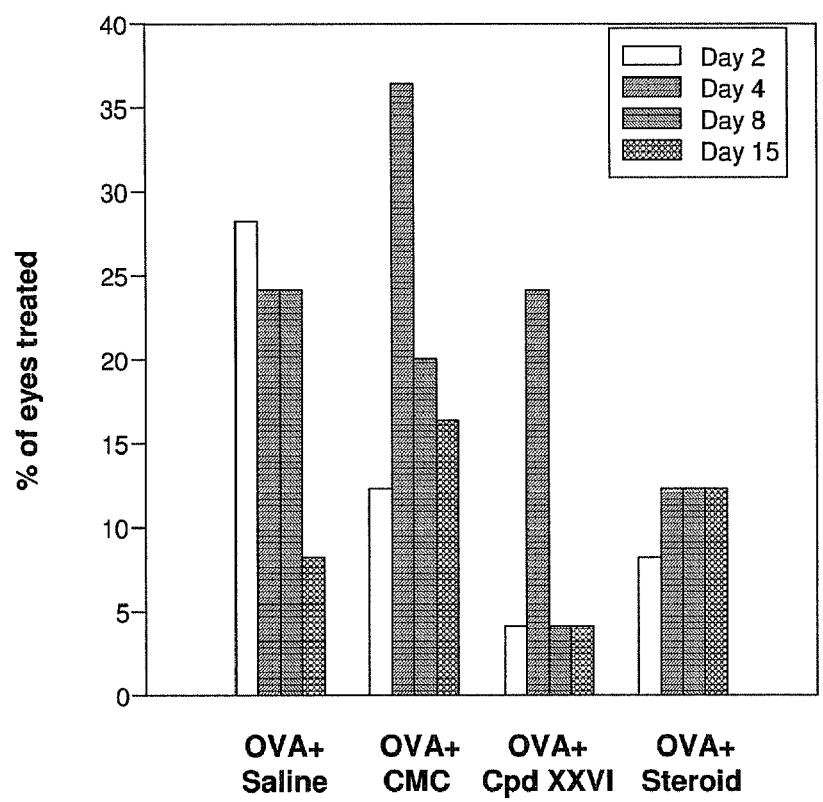

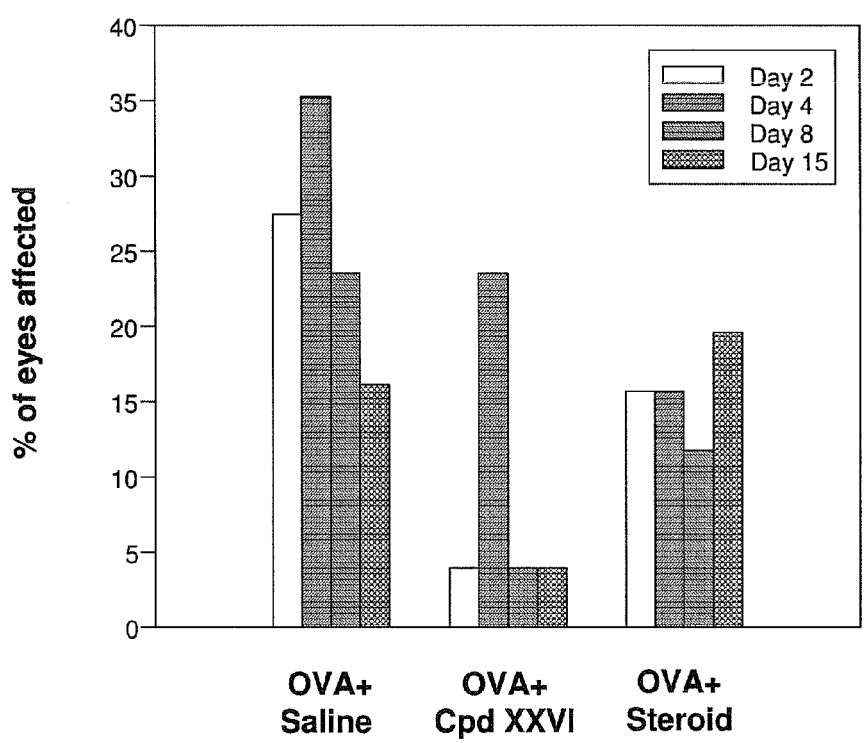
Fig. 2: Effect of Compound XXVI on allergic conjunctivitis in guinea pigs. Corneal opacities at the late post-provocation phase.

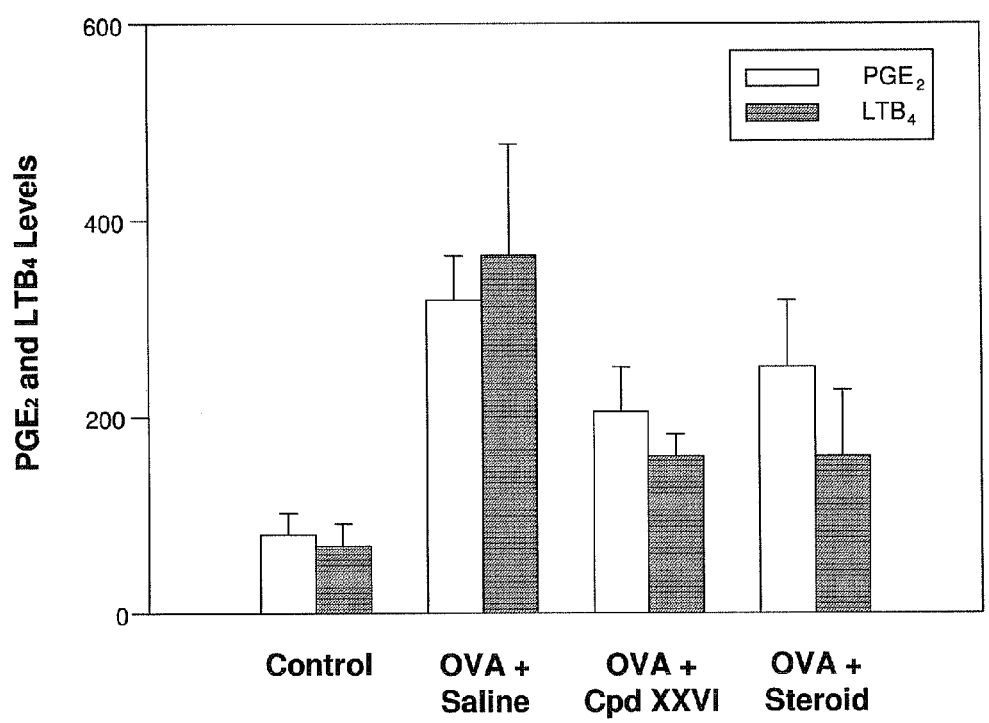
Fig. 3: Effect of Compound XXVI on prostaglandin $E_2$ ($PGE_2$) and leukotriene $B_4$ ($LTB_4$) levels in the cornea of guinea pigs with allergic conjunctivitis.

Fig. 4: Effect of Lipid-conjugates on HIV infectivity
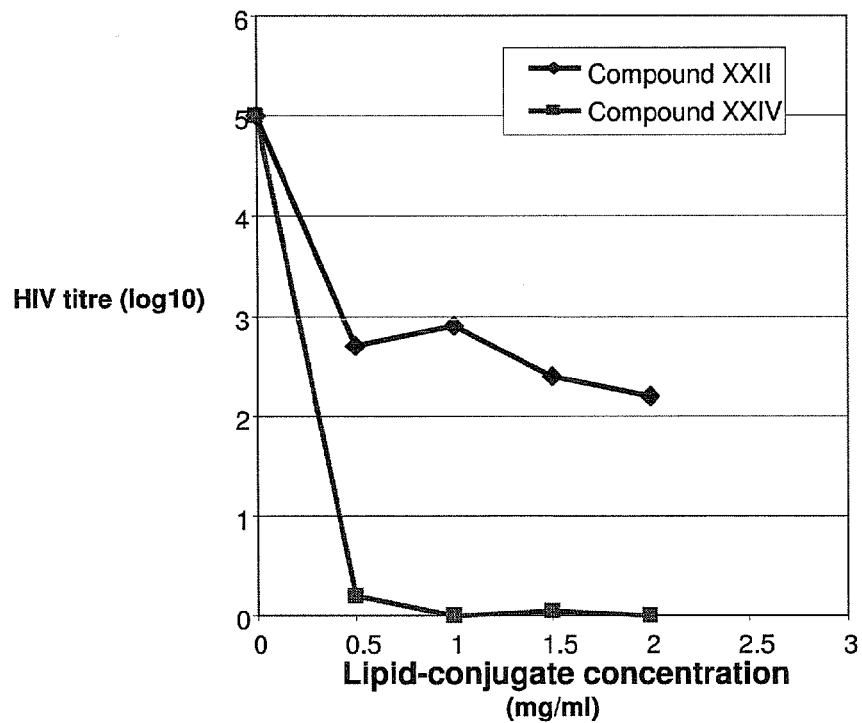
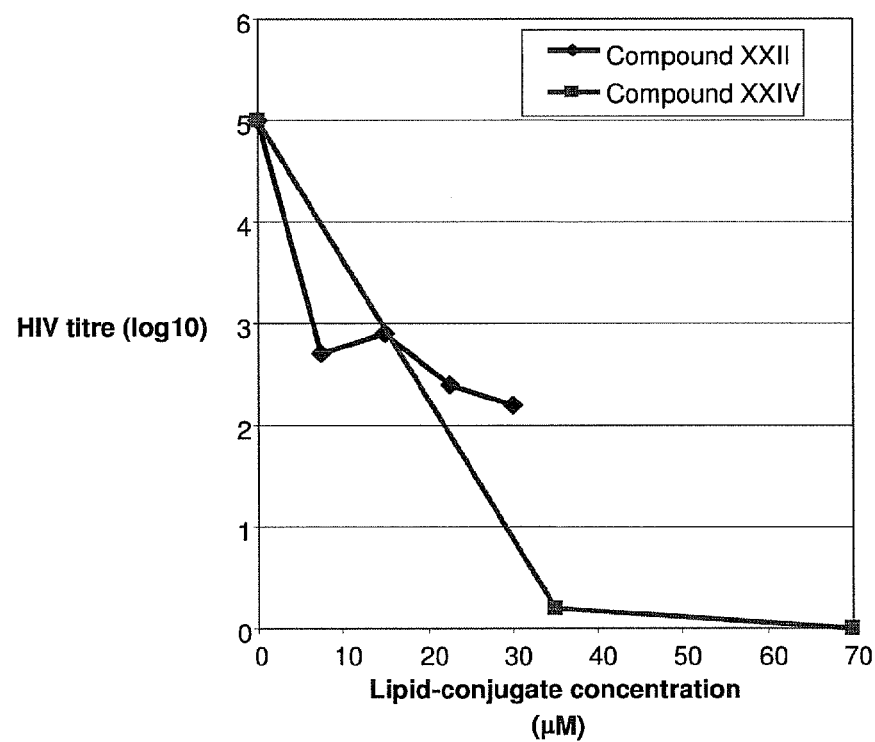

Fig. 5: Effect of Lipid-conjugates on infection of HeLa cells by *Chlamydia*.

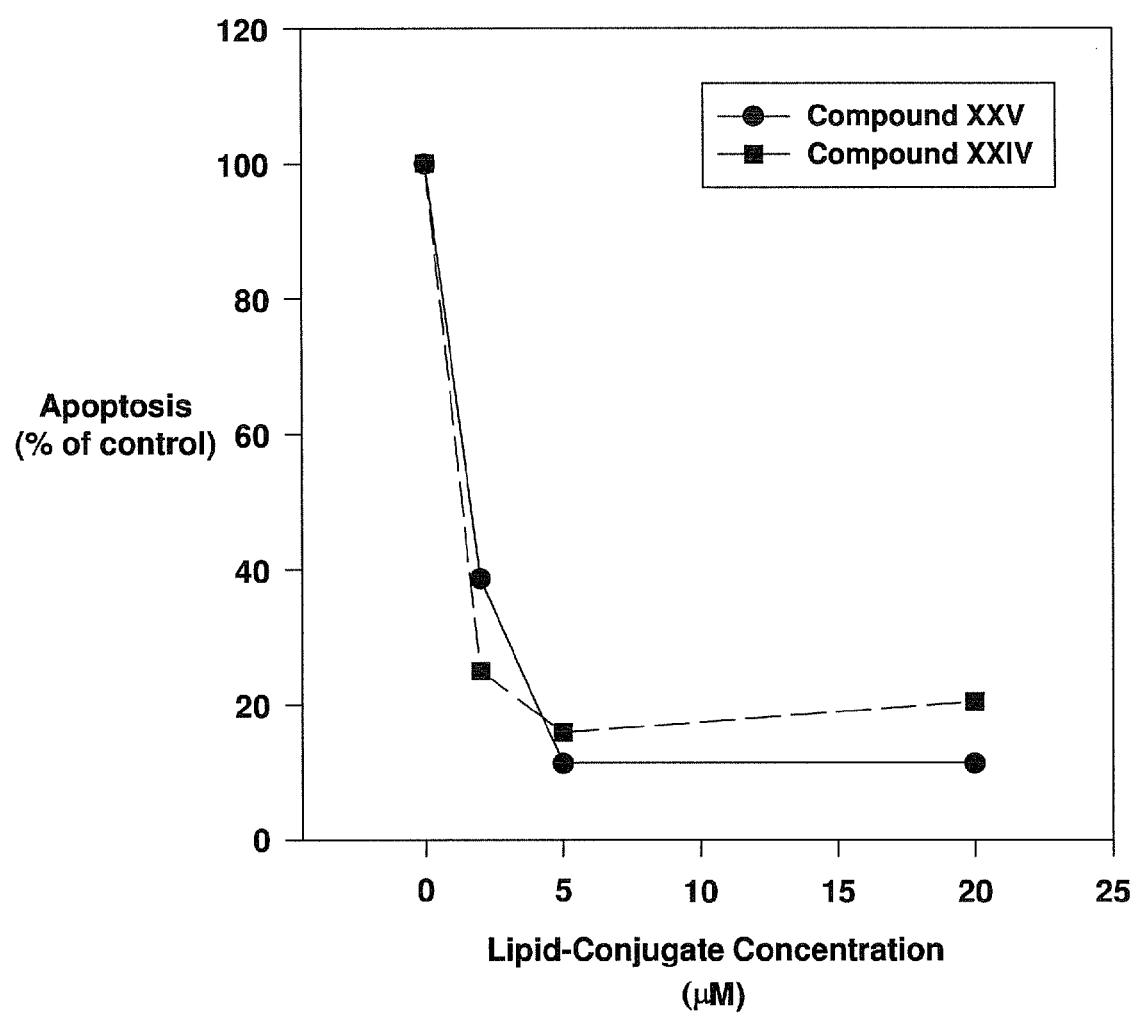
Fig. 6: Effect of Lipid-conjugates on *Chlamydia*-induced apoptosis of HeLa cells.

Fig. 7: Compound (Cpd) XXVI protects BGM cells from membrane lysis induced by combined action of hydrogen peroxide produced by glucose oxidase (GO) and exogenous phospholipase $A_2$ ($PLA_2$).
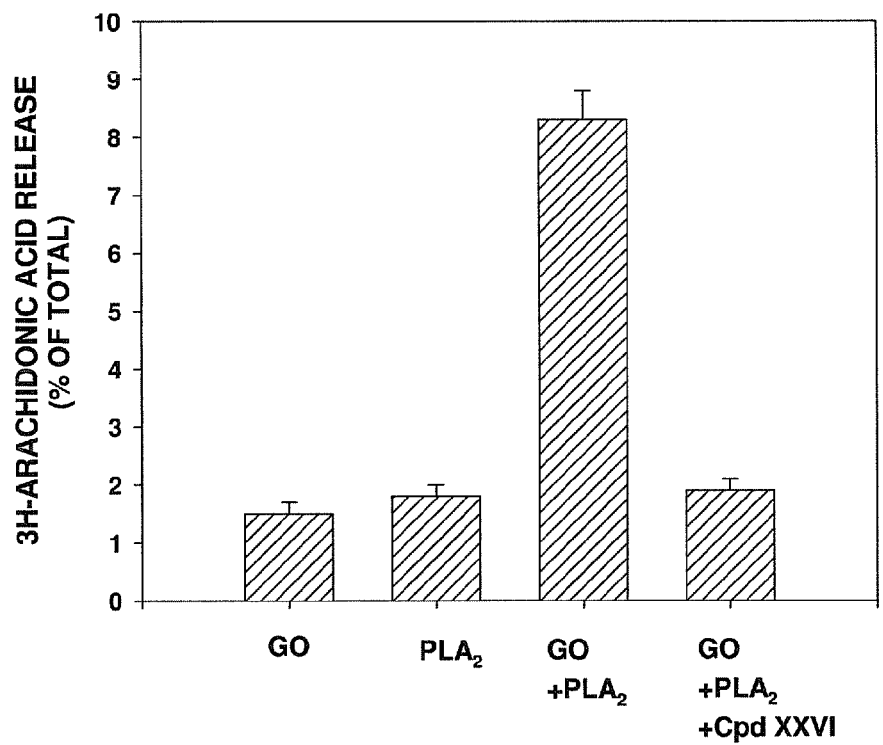

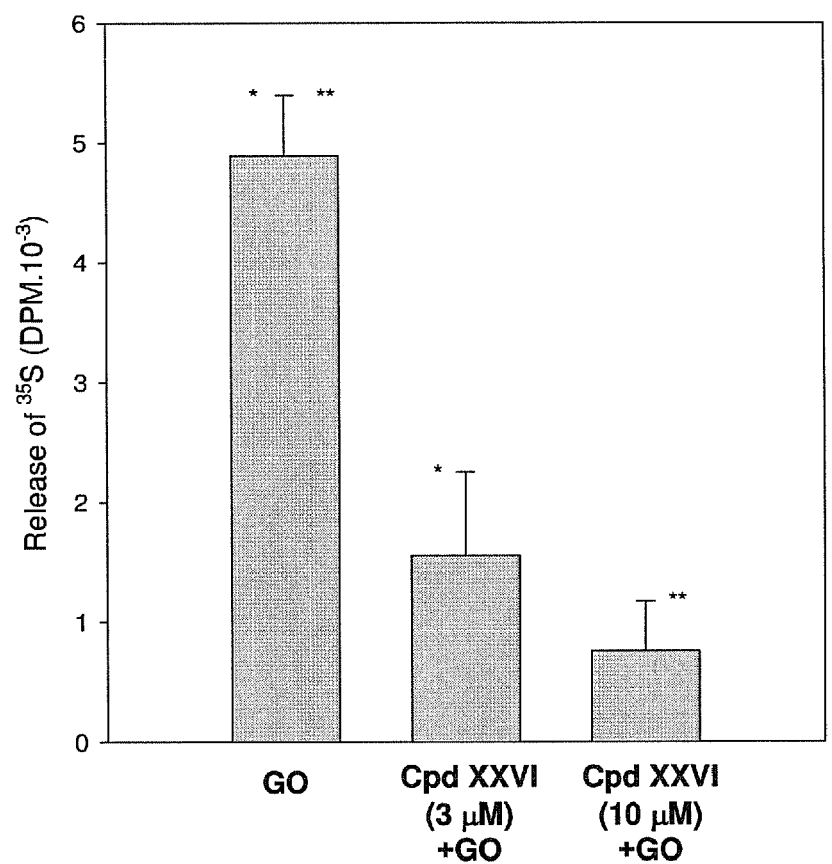
Fig. 8: Compound (Cpd) XXVI protects BGM cells from glycosaminoglycan degradation by hydrogen peroxide produced by glucose oxidase (GO).

Fig. 9: Compound XXII protects LDL from copper-induced oxidation.
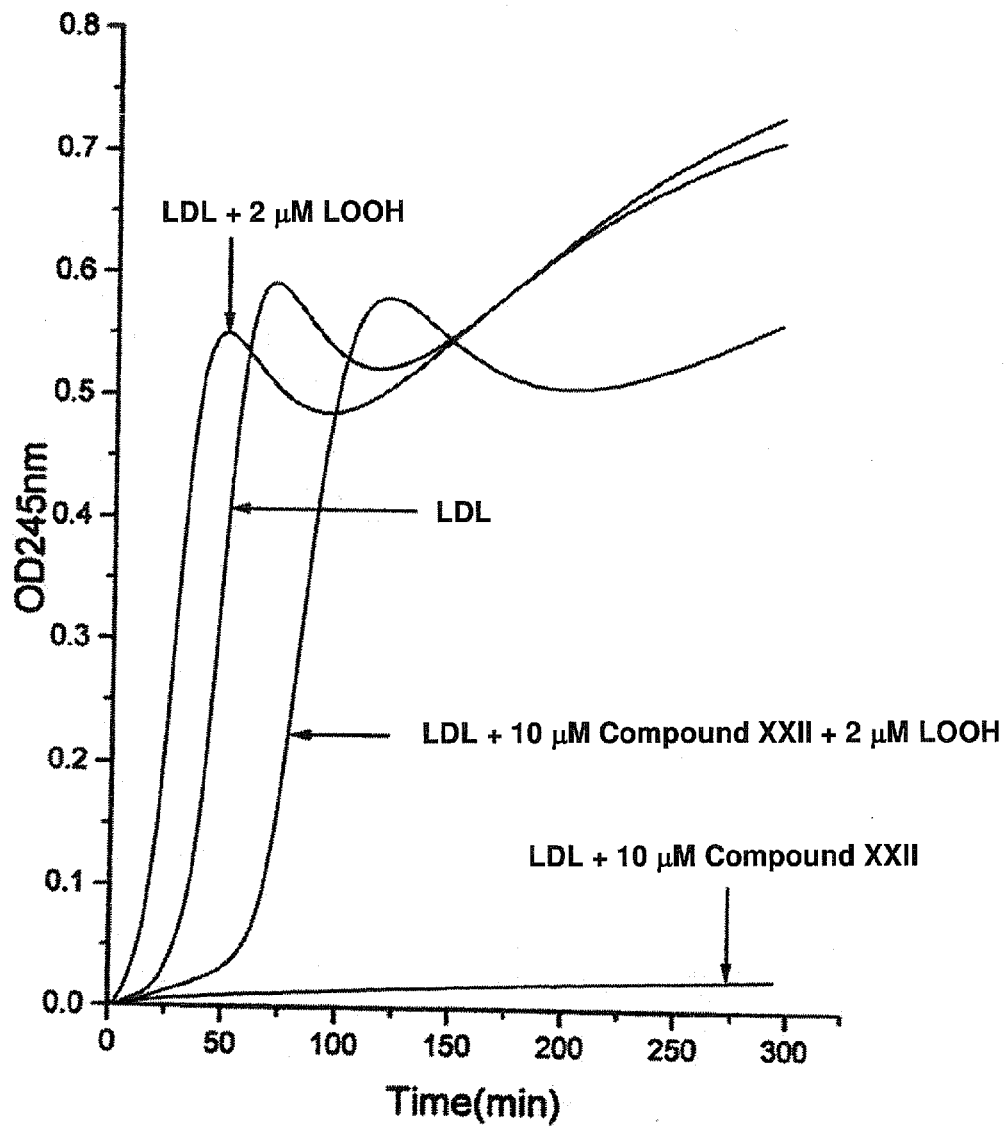

Fig. 10: Effect of Compound XXVI on the proliferation of cultured human psoriatic fibroblasts and Swiss 3T3 cells.
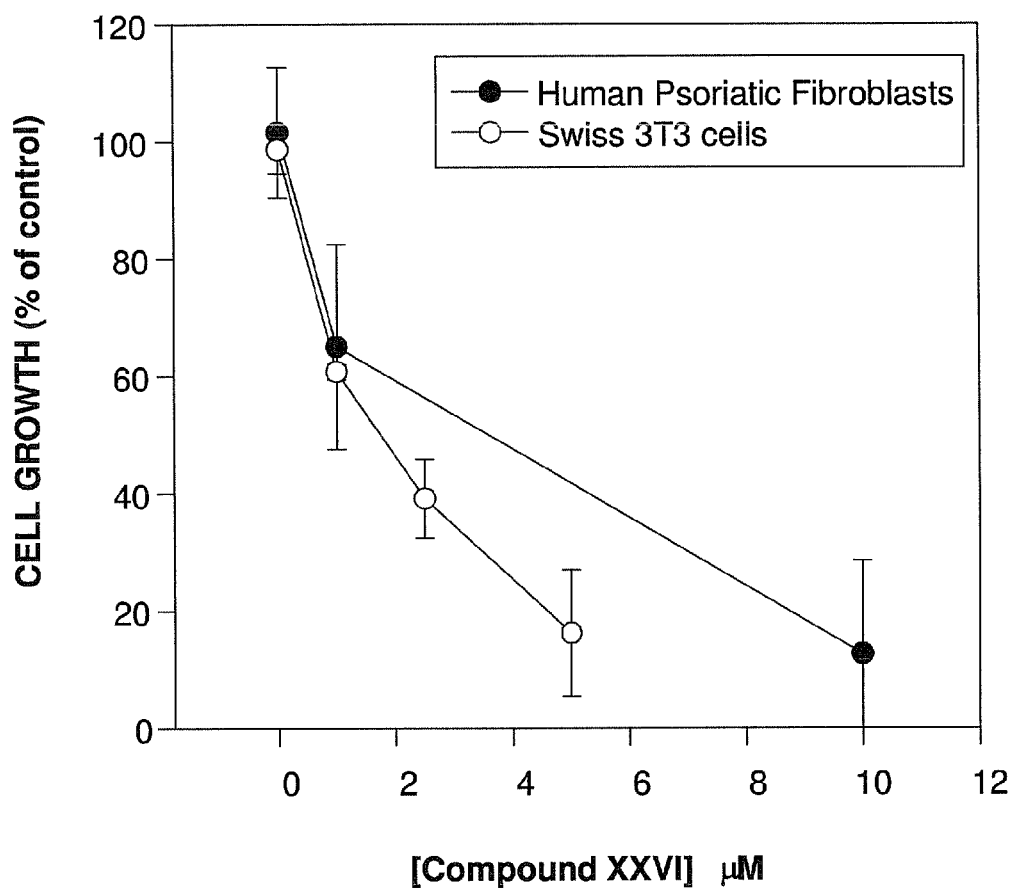

Fig. 11: Improvement of contact dermatitis score in patients on vehicle- and Compound XXII -treated sides
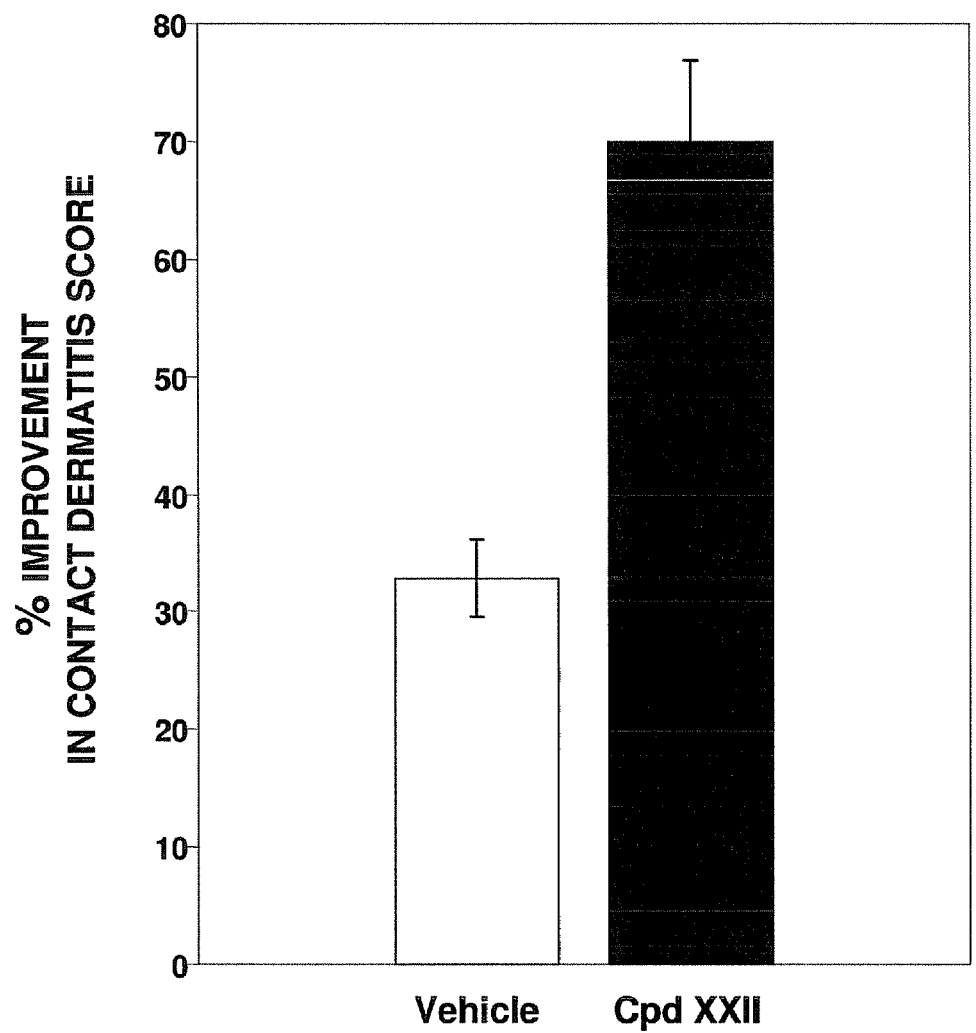

Fig. 12: Inhibition of the PLA$_2$ enzyme by Compound XXII
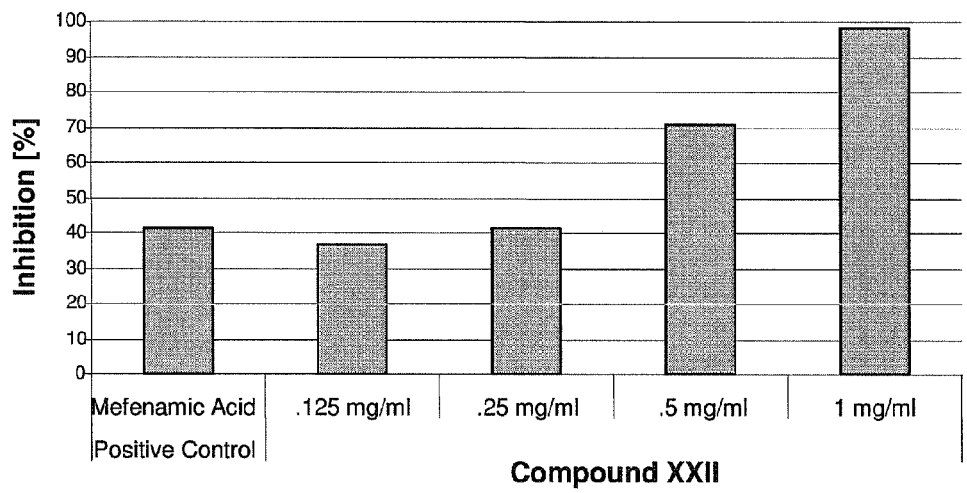
Fig. 13: Inhibition of the PLA$_2$ enzyme by Compound XXV
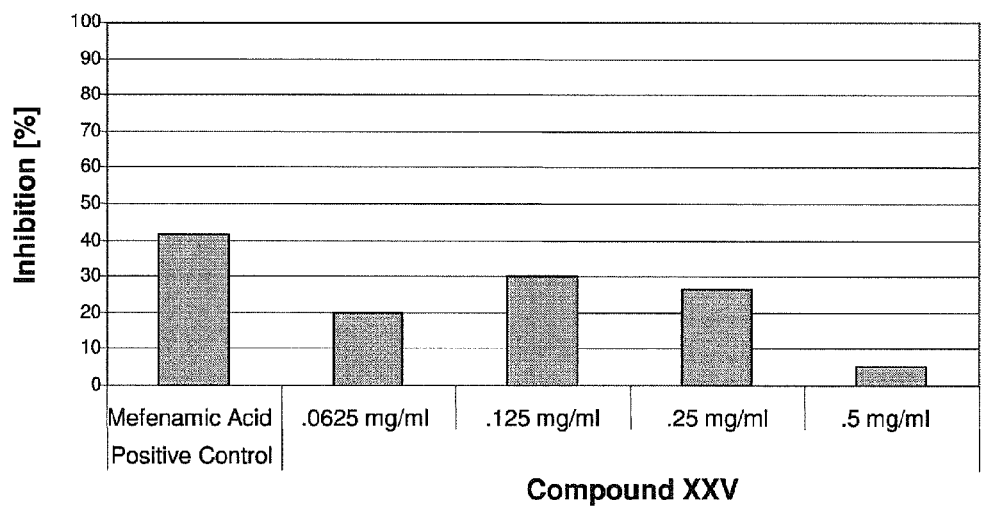

acceptable monomer, dimer, oligomer, or polymer, in the preparation of a composition for treating a subject afflicted with conjunctivitis.

In one embodiment, the term "conjunctivitis" refers to an inflammation of the outermost layer of the eye, the inner surface of the eyelids, or both. In one embodiment, "conjunctivitis" refers to any one or more of the following conditions: acute conjunctivitis, chronic conjunctivitis, bacterial conjunctivitis, nongonococcal bacterial conjunctivitis, adult gonococcal conjunctivitis, inclusion conjunctivitis, chlamydial conjunctivitis, rickettsial conjunctivitis, fungal conjunctivitis, parasitic conjunctivitis, viral conjunctivitis, immunologic conjunctivitis, iatrogenic conjunctivitis, giant papillary conjunctivitis, hay fever conjunctivitis, seasonal allergic conjunctivitis, keratoconjunctivitis, epidemic keratoconjunctivitis, vernal keratoconjunctivitis, atopic conjunctivitis, atopic keratoconjunctivitis, acute hemorrhagic conjunctivitis, pharyngoconjunctival fever, phlyctenulosis (phlycentular keratoconjunctivitis), blepharoconjunctivitis, acute epidemic conjunctivitis, pinkeye, inclusion blennorrhea of the newborn, swimming pool conjunctivitis, trachoma, granular conjunctivitis, egyptian ophthalmia, keratitis (corneal ulcer), or a combination thereof.

In one embodiment, "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of conjunctivitis, while in one embodiment, "secondary" refers to a symptom that is derived from or consequent to a primary cause. In one embodiment, the compounds for use in the present invention treat primary or secondary symptoms or secondary complications related to conjunctivitis.

In another embodiment, "symptoms" may be any manifestation of a disease or pathological condition, comprising inflammation, swelling, fever, pain, bleeding, itching, runny nose, coughing, headache, migraine, dizziness, blurry vision, etc., or a combination thereof. In one embodiment, symptoms comprise itchy eyes, swollen eyelids, redness, irritation, watery eyes, mucoid discharge, pain, or a combination thereof.

In one embodiment, the invention provides the use of compounds of the present invention to suppress, inhibit, prevent, or treat eye irritation.

In another embodiment, the invention provides for the use of the described compounds to suppress, inhibit, prevent or treat diseases, disorders or conditions associated with conjunctivitis in a subject. In some embodiments, such diseases, disorders or conditions are a by-product of conjunctivitis, for example, systemic infection, as a result of spread from the initial focus of infection. Another example, and embodiment of this invention, is dermatitis at a region proximal to the affected eye, as a consequence of, for example, rubbing and itching, due to conjunctivitis in the subject, and others as will be appreciated by one skilled in the art.

In one embodiment, the methods of the present invention prevent or treat to symptoms of conjunctivitis, including, inter alia, conjunctival injection, conjunctival hyperemia, watery discharge, tearing, lacrimation, serous discharge, stringy discharge, thick mucopurulent discharge, ocular irritation, discomfort, ocular itch, photophobia, edematous eyelids, pinpoint subconjunctival hemorrhages, pseudomembrane formation and palpable preauricular lymph nodes.

In some embodiments, the methods of the present invention prevent or treat conjunctival desiccation, which may cause scarring and symblepharon formation (adherence of the bulbar and palpebral conjunctivas), in one embodiment. In one embodiment, the methods of the present invention treat penetration of an intact cornea.

In one embodiment, the methods of the present invention treat symptoms of conjunctivitis caused by epidemic keratoconjunctivitis (EKC) or pharyngoconjunctival fever (PCF). In one embodiment, symptoms of EKC comprise bilateral, inferior, palpebral, follicular conjunctivitis, with epithelial and stromal keratitis or subepithelial corneal infiltrates. In one embodiment, the pathogen causing EKC is adenovirus type 8 adenovirus type 19, adenovirus type 37, adenovirus type 5, or a combination thereof. In one embodiment, symptoms of PCF comprise fever, sore throat and follicular conjunctivitis. In one embodiment, the pathogen causing PCF is adenovirus type 3, adenovirus type 4, adenovirus type 7, or a combination thereof.

In one embodiment, the methods of the present invention treat nongonococcal bacterial conjunctivitis, which in one embodiment, is caused by *Staphylococcus aureus, Streptococcus pneumoniae*, or *Haemophilus influenzae*. In another embodiment, the methods of the present invention treat gonococcal conjunctivitis, which in one embodiment, is caused by *Neisseria gonorrhoeae*. In another embodiment, the methods of the present invention treat inclusion conjunctivitis, which in one embodiment, is caused by *Chlamydia trachomatis*, which in one embodiment comprise serotypes D-K. In one embodiment, symptoms include lid swelling, chemosis and mucopurulent discharge.

Thus, in one embodiment of the present invention, the compounds for use in the present invention are directed towards the resolution of symptoms of conjunctivitis. In another embodiment, the compounds affect the pathogenesis underlying conjunctivitis.

In one embodiment, the present invention provides methods of treating conjunctivitis, which in one embodiment, can be caused or exacerbated by microbial or pathogenic infections, which in one embodiment are viral and in another embodiment are bacterial. In one embodiment, conjunctivitis is due to an infection of a cell by a pathogen. In one embodiment, the pathogen is a virus and in another embodiment, the pathogen is a bacterium.

In one embodiment, conjunctivitis may affect a cell, in one embodiment, a vertebrate cell, in another embodiment, a mammalian cell, and in another embodiment, a human cell. It is to be understood that compounds of the present invention may be efficacious in treating any cell type in which conjunctivitis or the causes of conjunctivitis may exert an effect. In one embodiment, a compound for use in the present invention may localize to or act on a specific cell type. In one embodiment, a compound for use in the present invention may be cytoprotective. In one embodiment a compound for use in the present invention may be inserted or partially inserted into a cell membrane. In another embodiment a compound for use in the present invention may be effective in treating a plurality of cell types.

In another embodiment, conjunctivitis is a primary or secondary effect of an infection mediated by any one or more of the following bacterial pathogens: *Neisseria, Neisseria gonorrhoeae, Neisseria meningitidis, Streptococcus pneumoniae, Streptococcus pyogenes, Staphylococcus aureus, Staphylococcus epidermidis, Moraxella lacunata, Haemophilus, Haemophilus aegyptus, Haemophilus influenzae, Pseudomonas, Pseudomonas aeruginosa, Listeria monocytogenes, Acinetobacter lwoffi, Bacillus cereus*. In another embodiment, conjunctivitis is a primary or secondary effect of an infection mediated by any one or more of the following bacterial pathogens: *Branhamella (Neisseria) catarrhalis, Corynebacterium, Corynebacterium diphtheriae, Mycobacterium tuberculosis, Mycobacterium fortuitum, Treponema pallidum, Coliforms, Proteus*. In another embodiment, conjunctivitis is a primary or secondary effect of an infection mediated by any one or more of the following bacterial pathogens: *Chlamydia trachomatis* (Trachoma), *Chlamydia oculogenitalis* (inclusion conjunctivitis), *Chlamydia lymphogranulomatis* (Lymphogranuloma venereum), *Chlamydia psittaci* (Psittacosis).

In another embodiment, conjunctivitis is a primary or secondary effect of an infection mediated by micro-organisms of the family Rickettsiaceae, comprising: *Rickettsia prowazekii* (epidemic typhus), *R. typhi* (endemic typhus), *R. tsutsugamushi* (scrub typhus), *R. rickettsii* (Rocky Mountain Spotted Fever), *R. conorii* (Mediterranean is Fever), *R.* (*Coxiella*) *burnetii* (Q Fever).

In another embodiment, conjunctivitis is a primary or secondary effect of an infection mediated by any one or more of the following viral pathogens: Adenovirus, Adenovirus type 3, Adenovirus type 4, Adenovirus type 7, Adenovirus type 8; picornavirus, enterovirus 70, Coxsackie A24, enterovirus, enterovirus type 8, enterovirus type 19, Herpes Simplex Virus, Herpes simplex virus type one, Herpes simplex virus type two, Herpes simplex virus type three (Herpes Varicella-Zoster Virus), Herpes simplex virus type five (cytomegalovirus), Enterovirus type 70, Coxsackie virus type A28, poxvirus, which in one embodiment may be molluscum contagiosum or vaccinia, Varicella Zoster, rhinovirus, influenza virus, Influenza Type A virus, which in one embodiment is H7N7, H1N1, H2N2, H3N2, or H5N1, Influenza Type B virus, Influenza Type C virus, avian influenza, or swine influenza.

In another embodiment, conjunctivitis is a primary or secondary effect of an infection mediated by any one or more of the following viral pathogens: pneumoencephalitis (Newcastle disease), Epstein-Barr virus, papilloma virus, dengue fever, vaccinia virus.

In another embodiment, conjunctivitis is a primary or secondary effect of an infection mediated by any one or more of the following pathogens: paramyxovirus, which in one embodiment is measles virus, mumps virus, or Newcastle virus, rubella virus, rubeola virus, *Treponema pallidum, Brucella, Borrelia burgdorferi*, Human immunodeficiency virus, *Leptospira interrogans, Toxocara, Crytococcus neoformans, Histoplasma capsulatum, Myobacterium tuberculosis*.

In another embodiment, conjunctivitis is a primary or secondary effect of an infection mediated by any one or more of the following parasitic pathogens: *Philophthalmus lacrimosus, Pediculus pubis, Onchocerca volvulus, Thelazia, Thelazia californiensis, Loa Loa, Ascaris lumbricoides, Trichinella spiralis, Schistosoma haematobium, Taenia solium, Wuchereria bancrofti, Echinococcus*.

In another embodiment, conjunctivitis is a primary or secondary effect of an infection mediated by any one or more of the following fungal pathogens: *Rhinosporidium seeberi, Coccidioides immitis, Sporothrix schenkii, Aspergillus, Allescheria, Mucor*, Dermatophytes (*Microsporum, Epidermophyton, Trichophyton*), *Candida, Candida albicans*.

In one embodiment, conjunctivitis or persistant conjunctivitis is a primary or secondary symptom of an underlying illness, which in one embodiment, is an autoimmune disease. In one embodiment, the underlying illness is rheumatoid arthritis, systemic lupus erythematosus, Kawasaki's Disease, ulcerative colitis, Crohn's Disease, sarcoidosis, etc, or any combination thereof.

In another embodiment, conjunctivitis is a primary or secondary effect of exposure to an allergen. In one embodiment, conjunctivitis is due to an immediate hypersensitivity reaction and in another embodiment, to a delayed hypersensitivity reaction. In one embodiment, allergens may be any one or more of the following: pollen, grass, ragweed, animal dander, dust mites, mold spores, cosmetics, perfume, contact lens solution, or chemicals.

In one embodiment, conjunctivitis is a primary or secondary effect of exposure to an irritant, which may be any one or more of the following: cosmetics, perfumes, skin medicines, air pollution, dust, dirt, eyelashes, wind, contact lenses, protein deposits on contact lenses, contact lens solutions, an artificial eye, environmental irritants, cigarette smoke, chemicals, industrial chemicals, household chemicals, strongly alkaline materials, toxins, ricin, castor oil, soap, shampoo, chlorinated pool water, surgical suture, foreign object in eye, irritant plant saps, irritant gases, toxins, natural toxins, strongly alkaline materials, intense ultraviolet light, sunlamps, reflection from snow.

In another embodiment, conjunctivitis is a primary or secondary effect of long term therapeutic administration of topically applied drugs or solutions to the affected eye. In one embodiment, such drugs or solutions may comprise miotics, neomycin, idoxuridine, contact lens solutions, eyedrops, eye ointments.

In another embodiment, conjunctivitis is a primary or secondary effect of thermal or ultraviolet burns, epithelial dysplasia, sarcoidosis, Xerophthalmia, aging, overuse of contact lenses, foreign bodies, vitamin deficiency, vitamin A deficiency, dry eye, dryness due to inadequate lid closure, scarring from previous injury, or autoimmune diseases such as rheumatoid arthritis.

In one embodiment, the methods of the present invention may be used to treat conjunctivitis acquired via zoonotic transmission. In one embodiment, the methods of the present invention may be used to treat conjunctivitis acquired from avian, swine, bovine, or bat. In another embodiment, the methods of the present invention may be used to treat conjunctivitis resulting from exposure to chickens with Newcastle disease. In another embodiment, the methods of the present invention may be used to diminish pathogen reservoirs in animal species.

In one embodiment, the methods of the present invention may be used to treat conjunctivitis in a subject that is immunosuppressed, while in another embodiment, in a subject that is immunodeficient.

In one embodiment, the compounds for use in the present invention (for e.g., a lipid or phospholipid moiety bound to a physiologically acceptable monomer, dimer, oligomer, or polymer) are referred to herein as "Lipid-conjugates".

In one embodiment, this invention provides for the use of Lipid-conjugates to suppress, inhibit, prevent, or treat conjunctivitis. In another embodiment, this invention provides for the use of Lipid-conjugates to suppress, inhibit, prevent, or treat allergic conjunctivitis. Treatment of conjunctivitis is exemplified in FIGS. 1, 1B, and 1C and represents an embodiment of this invention. In another embodiment, this invention provides for the use of Lipid-conjugates to decrease corneal opacity at the immediate post-provocation phase (as exemplified in FIG. 1), or in another embodiment, to decrease corneal opacity at the late post-provocation phase (as exemplified in FIG. 4). In another embodiment, this invention provides for the use of Lipid-conjugates to decrease inflammatory modulators, such as $PGE_2$ and $LTB_4$ (as exemplified in FIG. 3). In one embodiment, this invention provides for the use of Compound XXVI to treat conjunctivitis. In another embodiment, this invention provides for the use of Compound XXVI to decrease corneal opacity at the immediate post-provocation phase, or in another embodiment, at the late post-provocation phase, or in another embodiment, to decrease inflammatory modulators, such as $PGE_2$ and $LTB_4$, or any combination thereof, some of which are exemplified herein in FIGS. 1A-1C.

In one embodiment, the invention provides a method for treating a subject with conjunctivitis associated with inflammation, an inappropriate cytokine response, or a combination thereof. In another embodiment, local cytokine profiles can be altered by the treatment according to the methods of the present invention. In one embodiment, the determination of the modulation of cytokines may be performed as described by U.S. application Ser. No. 10/952,496 filed Sep. 29, 2004, which is incorporated herein by reference in its entirety.

In one embodiment, the methods of the present invention may be used to prevent or treat episcleritis, which in one embodiment, is an inflammation of the episcleral tissues, which in one embodiment, may be recurring. In one embodiment, treatment according to this invention, may include administration of the compounds as herein described, with the onset of the following symptoms in the subject, such as, but not limited to: localized conjunctival hyperemia, tenderness, irritation, mild photophobia, and/or some lacrimation. In another embodiment, symptoms may include the appearance of a bright red patch present just under the bulbar conjunctiva (simple episcleritis), or a hyperemic, edematous, raised nodule (nodular episcleritis). In one embodiment, the methods of the present invention may be used to prevent or treat scleritis, which in one embodiment, is diffuse scleritis, nodular scleritis, or necrotizing scleritis and which, in another embodiment, is a severe, destructive, vision-threatening inflammation involving the deep episclera and sclera. In one embodiment, symptoms of episcleritis usually include pain (most often characterized as a deep, boring ache) that often interferes with sleep and appetite, tenderness, photophobia, lacrimation, and localized or generalized conjunctival hyperemia.

In one embodiment, the methods of the present invention may be used to suppress, prevent or treat Cicatricial Pemphigoid, Ocular Cicatricial Pemphigoid, Benign Mucous Membrane Pemphigoid, which, in one embodiment, refers to a chronic, bilateral, progressive scarring and shrinkage of the conjunctiva with opacification of the cornea. In one embodiment, "Cicatricial pemphigoid" refers to an autoimmune disease in which binding of anticonjunctival basement membrane antibodies results in inflammation. In another embodiment, the methods of the present invention may be used to prevent or treat symblepharon (scarring of the palpebral conjunctiva to the globe); trichiasis (inturning eyelashes); keratitis sicca; corneal neovascularization, opacification, and keratinization; conjunctival shrinkage and keratinization; and blindness.

In another embodiment, the methods of the present invention include treatment of conditions associated with secondary infections, which in some embodiments, result in conjunctivitis in a subject.

Administration of the Lipid-conjugates was exemplified herein as a means to reduce early and late post-provocation corneal opacity and ophthalmic levels of leukotriene B4 and prostaglandin E2 after induction of delayed-type hypersensitivity conjunctivitis in guinea pigs (as exemplified in Example 1). Lipid-conjugates have been shown to be effective in treating viral and/or bacterial infection, which in some embodiments, causes conjunctivitis (as exemplified in Examples 2 and 3). In one embodiment, the Lipid-conjugates for use according to the methods of this invention, may also prevent and/or treat conjunctivitis via their membrane-stabilizing effects (as exemplified in Examples 4 and 5) and/or via protecting against oxidative injury (as exemplified in Example 5). The Lipid-conjugates for use according to the methods of this invention have been shown to decrease DTH-induced ear swelling whether applied ip, sc, or topically, to inhibit the proliferation of cultured psoriatic skin fibroblasts and Swiss 3T3 cells, and improve dermatitis score (as exemplified in Example 6) which, in some embodiments, is a mechanism whereby they are useful in treating, preventing, or suppressing conjunctivitis. The Lipid-conjugates for use according to the methods of this invention have been shown, in some embodiments, to prevent or treat conjunctivitis via their $PLA_2$ enzyme inhibitory activity (as exemplified in Example 7), which, in some embodiments, is a mechanism whereby they are useful in treating, preventing, suppressing, etc. conjunctivitis.

The compounds for the use according to the methods of this invention may reduce sPLA2 expression, reduce cysteinyl leukotrienes, reduce or inhibit NO production, reduce tumor necrosis factor-α (TNF-α) reduce PGE2, sPLA2, and oleic acid release; reduce IL-8, Gro-α, ena-78, and/or NF-κB (as exemplified in U.S. application Ser. No. 10/952,496, which is incorporated by reference herein), or any combination thereof, which in turn may represent a mechanism whereby the compounds are useful in treating, preventing, suppressing, etc. conjunctivitis in a subject.

In one embodiment of the invention, the mechanism whereby the use of the Lipid-conjugates described herein can be used to treat conjunctivitis, involves amelioration, or prevention, of tissue injury arising in the course of pathological disease states by stabilizing cell membranes; limiting oxidative damage to cell and blood components; or attenuating physiological reactions to stress, as expressed in elevated chemokine levels.

In some embodiments of the invention, the compounds for use according to the methods of this invention have an efficacy, or other desirable characteristics, which are useful in the treatment, prevention and/or suppression of conjunctivitis, which exceeds that of the starting materials alone, or when administered unconjugated, but in combination.

In one embodiment, methods of the present invention involve treating a subject by inter alia controlling the expression, production, and activity of phospholipases such as PLA2; controlling the production and/or action of lipid mediators, such as eicosanoids, platelet activating factor (PAF) and lyso-phospholipids; amelioration of damage to cell surface glycosaminoglycans (GAG) and proteoglycans; controlling the production of oxidants, oxygen radicals and nitric oxide; protection of cells, tissues, and plasma lipoproteins from damaging agents, such as reactive oxygen species (ROS) and phospholipases; controlling the expression, production, and activity of cytokines, chemokines and interleukins; anti-oxidant therapy; anti-endotoxin therapy or any combination thereof, via the administration of the described compounds and compositions comprising the same.

In one embodiment of the invention, the term "controlling" refers to inhibiting the production and action of the above mentioned factors in order to maintain their activity at normal basal levels and suppress their activation in pathological conditions.

In one embodiment of the invention, conjunctivitis is characterized by the presence of damaging agents, which comprise, inter alia, phospholipases, reactive oxygen species (ROS), free radicals, lysophospholipids, fatty acids or derivatives thereof, hydrogen peroxides, phospholipids, oxidants, cationic proteins, streptolysins, proteases, hemolysins, or sialidases.

Dosages and Routes of Administration

This invention encompasses administration of compounds as described herein or compositions comprising the same, for treating conjunctivitis.

In one embodiment, compositions of this invention are pharmaceutically acceptable. In one embodiment, the term "pharmaceutically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration.

In one embodiment, a Lipid-conjugate used in the methods of this invention may be administered alone or within a composition. In another embodiment, compositions comprising Lipid-conjugates in admixture with conventional excipients, i.e. pharmaceutically acceptable organic or inorganic carrier substances suitable for parenteral, enteral (e.g., oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g., vitamins.

In one embodiment, the therapeutic compositions of the instant invention comprise a Lipid-conjugate and additional compounds effective in preventing or treating conjunctivitis. In one embodiment, the additional compounds comprise anti-inflammatory compositions, which in one embodiment are non-steroidal anti-inflammatory medications, antihistamines, antibiotics, corticosteroids, cromolyn sodium (sodium cromoglicate), mast-cell stabilizers, artificial tears, lubricants, or a combination thereof. In one embodiment, antibiotics comprise chloramphenicol, fusidic acid, tetracycline, erythromycin, gentamycin, or a combination thereof. In another embodiment, an additional compound is vitamin A.

In one embodiment, the therapeutic compositions of the instant invention are administered with other treatments that relieve symptoms. In one embodiment, other treatments comprise application of cold compresses, while in another embodiment, warm compresses.

In one embodiment, the route of administration may be parenteral, enteral, or a combination thereof. In another embodiment, the route may be intra-ocular, conjunctival, topical, transdermal, intradermal, subcutaneous, intraperitoneal, intravenous, intra-arterial, vaginal, rectal, intratumoral, parcanceral, transmucosal, intramuscular, intravascular, intraventricular, intracranial, inhalation, nasal aspiration (spray), sublingual, oral, aerosol or suppository or a combination thereof. In one embodiment, the dosage regimen will be determined by skilled clinicians, based on factors such as exact nature of the condition being treated, the severity of the condition, the age and general physical condition of the patient, etc.

For intra-ocular application, eye drops, ointments, lotions, creams, or coated eye patches may be used in one embodiment.

For parenteral application, particularly suitable are injectable, sterile solutions, preferably oily or aqueous solutions, as well as suspensions, emulsions, or implants, including suppositories and enemas. Ampoules are convenient unit dosages. Such a suppository may comprise any agent described herein.

For application by inhalation, solutions or suspensions of the compounds mixed and aerosolized or nebulized in the presence of the appropriate carrier suitable. Such an aerosol may comprise any agent described herein and, in one embodiment, may be used to treat diseases or conditions caused by airborne pathogens, which may in one embodiment, cause sinusitis or upper respiratory infections, in addition to conjunctivitis.

For topical application, particularly in the area around the eye, an admixture of the compounds with conventional creams, lotions, or delayed release patches is acceptable. Such a cream or lotion may comprise any agent described herein, and, in one embodiment, may be used to treat conjunctivitis.

For enteral application, particularly suitable are tablets, dragees, liquids, drops, or capsules. A syrup, elixir, or the like can be used when a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

Thus, in one embodiment, the route of administration may be directed to an organ or system that is affected by conjunctivitis. For example, compounds may be administered in intra-ocular form to treat conjunctivitis. In another embodiment, the route of administration may be directed to a different organ or system than the one that is affected by conjunctivitis. For example, compounds may be administered parenterally to treat conjunctivitis. Thus, the present invention provides for the use of Lipid-conjugates to in various dosage forms suitable for administration using any of the routes listed hereinabove.

In general, the doses utilized for the above described purposes will vary, but will be in an effective amount to exert the desired effect. As used herein, the term "pharmaceutically effective amount" refers to an amount of a compound of formulae A and I-LXXXVII as described hereinbelow, which will produce the desired alleviation in symptoms or other desired phenotype in a patient. The doses utilized for any of the above-described purposes will generally be from 1 to about 1000 milligrams per kilogram of body weight (mg/kg), administered one to four times per day, or by continuous IV infusion. When the compositions are dosed topically or intraocularly, they will generally be in a concentration range of from 0.1 to about 10% w/v, administered 1, 2, 3, or 4 times per day. In another embodiment, 0.5 to 5%, and in another embodiment, 1-4%.

In one embodiment of the invention, the concentrations of the compounds will depend on various factors, including the nature of the condition to be treated, the condition of the patient, the route of administration and the individual tolerability of the compositions.

It will be appreciated that the actual preferred amounts of active compound in a specific case will vary according to the specific compound being utilized, the particular compositions formulated, the mode of application, and the particular conditions and organism being treated. Dosages for a given host can be determined using conventional considerations, e.g., by customary comparison of the differential activities of the subject compounds and of a known agent, e.g., by means of an appropriate, conventional pharmacological protocol.

In one embodiment, the compounds of the invention may be administered acutely for acute treatment of temporary conditions, or may be administered chronically, especially in the case of progressive, recurrent, or degenerative disease. In one embodiment, one or more compounds of the invention may be administered simultaneously, or in another embodiment, they may be administered in a staggered fashion. In one embodiment, the staggered fashion may be dictated by the stage or phase of the disease.

In one embodiment, the present invention offers methods for the treatment of disease based upon administration of lipids covalently conjugated through their polar head group to a physiologically acceptable chemical moiety, which may be of high or low molecular weight.

The present invention has been illustrated in terms of the anti-disease activity of Lipid-conjugates and methods of their use as pharmaceutical compositions in the treatment of disease. The following sections present some examples of the therapeutic Lipid-conjugate compounds for use in the present invention and their chemical preparation.

Compounds

In one embodiment, the compounds for use in the present invention comprise a lipid or phospholipid moiety bound to a physiologically acceptable monomer, dimer, oligomer, or polymer. In one embodiment, the lipid compounds (Lipid-conjugates) for use in the present invention are described by the general formula:

[phosphatidylethanolamine-Y]$n$-X

[phosphatidylserine-Y]$n$-X

[phosphatidylcholine-Y]$n$-X

[phosphatidylinositol-Y]$n$-X

[phosphatidylglycerol-Y]$n$-X

[phosphatidic acid-Y]$n$-X

[lyso-phospholipid-Y]$n$-X

[diacyl-glycerol-Y]$n$-X

[monoacyl-glycerol-Y]$n$-X

[sphingomyelin-Y]$n$-X

[sphingosine-Y]$n$-X

[ceramide-Y]$n$-X wherein
Y is either nothing or a spacer group ranging in length from 2 to 30 atoms; and
X is a physiologically acceptable monomer, dimer, oligomer or polymer; and
n is the number of lipid molecules bound to a molecule of X, wherein n is a number from 1 to 1000.

In one embodiment, the invention provides low-molecular weight Lipid-conjugates, previously undisclosed and unknown to possess pharmacological activity, of the general formula described hereinabove. In another embodiment, wherein the general formula described hereinabove describes low-molecular weight Lipid-conjugates, X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid.

In one embodiment of this invention, X is salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, a dipeptide, a disaccharide, a trisaccharide, an oligosaccharide, a polysaccharide, a hetero-polysaccharide, a homo-polysaccharide, a polypyranose, an oligopeptide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid, a glycosaminoglycan, polygeline ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid.

In one embodiment, X is conjugated to the lipid, phospholipid, or spacer via an ester bond. In another embodiment, X is conjugated to the lipid, phospholipid, or spacer via an amide bond.

As defined by the structural formulae provided herein for the Lipid-conjugates, these compounds may contain between one to one thousand lipid moieties bound to a single physiologically acceptable polymer molecule. In one embodiment of this invention, n is a number from 1 to 1000. In another embodiment, n is a number from 1 to 500. In another embodiment, n is a number from 1 to 100. In another embodiment, n is a number from 2 to 1000. In another embodiment, n is a number from 2 to 100. In another embodiment, n is a number from 2 to 200. In another embodiment, n is a number from 3 to 300. In another embodiment, n is a number from 10 to 400. In another embodiment, n is a number from 50 to 500. In another embodiment, n is a number from 100 to 300. In another embodiment, n is a number from 300 to 500. In another embodiment, n is a number from 500 to 800. In another embodiment, n is a number from 500 to 1000.

In one embodiment of the invention, when the conjugated moiety is a polymer, the ratio of lipid moieties covalently bound may range from one to one thousand lipid residues per polymer molecule, depending upon the nature of the polymer and the reaction conditions employed. For example, the relative quantities of the starting materials, or the extent of the reaction time, may be modified in order to obtain Lipid-conjugate products with either high or low ratios of lipid residues per polymer, as desired.

In one embodiment, the set of compounds comprising phosphatidylethanolamine covalently bound to a physiologically acceptable monomer, dimmer, oligomer, or polymer, is referred to herein as the PE-conjugates. In one embodiment, the phosphatidylethanolamine moiety is dipalmitoyl phosphatidylethanolamine. In another embodiment, the phosphatidylethanolamine moiety is dimyristoyl phosphatidylethanolamine. In another embodiment, related derivatives, in which either phosphatidylserine, phosphatidylcholine, phosphatidylinositol, phosphatidic acid or phosphatidylglycerol are employed in lieu of phosphatidylethanolamine as the lipid moiety provide equivalent therapeutic results, based upon the biological experiments described below for the Lipid-conjugates and the structural similarities shared by these compounds.

In another embodiment, the lipid or phospholipid moiety is phosphatidic acid, an acyl glycerol, monoacylglycerol, diacylglycerol, triacylglycerol, sphingosine, sphingomyelin, chondroitin-4-sulfate, chondroitin-6-sulfate, ceramide, phosphatidylethanolamine, phosphatidylserine, phosphatidylcholine, phosphatidylinositol, or phosphatidylglycerol, or an ether or alkyl phospholipid derivative thereof.

In one embodiment, Lipid-conjugate derivatives relevant to this invention are Lipid-conjugates wherein at least one of the fatty acid groups of the lipid moieties at position C1 or C2 of the glycerol backbone are substituted by a long chain alkyl group attached by amide, ether or alkyl bonds, rather than ester linkages.

In the methods, according to embodiments of the invention, the Lipid-conjugates administered to the subject are comprised from at least one lipid moiety covalently bound through an atom of the polar head group to a monomeric or polymeric moiety (referred to herein as the conjugated moiety) of either low or high molecular weight. When desired, an optional bridging moiety can be used to link the Lipid-conjugates moiety to the monomer or polymeric moiety. The conjugated moiety may be a low molecular weight carboxylic acid, dicarboxylic acid, fatty acid, dicarboxylic fatty acid, acetyl salicylic acid, cholic acid, cholesterylhemisuccinate, or mono- or di-saccharide, an amino acid or dipeptide, an oligopeptide, a glycoprotein mixture, a di- or trisaccharide monomer unit of a glycosaminoglycan such as a repeating unit of heparin, heparan sulfate, hyaluronic acid, chondroitin-sulfate, dermatan, keratan sulfate, or a higher molecular weight peptide or oligopeptide, a polysaccharide, a hetero-polysaccharide, a homo-polysaccharide, a polypyranose, polyglycan, protein, glycosaminoglycan, or a glycoprotein mixture. The composition of some phospholipid-conjugates of high molecular weight, and associated analogues, are the subject of U.S. Pat. No. 5,064,817, which is incorporated herein in its entirety by reference.

In one embodiment, the term "moiety" means a chemical entity otherwise corresponding to a chemical compound, which has a valence satisfied by a covalent bond.

In one embodiment, examples of polymers which can be employed as the conjugated moiety for producing Lipid-conjugates for use in the methods of this invention may be physiologically acceptable polymers, including water-dispersible or -soluble polymers of various molecular weights and diverse chemical types, mainly natural and synthetic polymers, such as glycosaminoglycans, hyaluronic acids, heparin, heparin sulfates, chondroitin sulfates, chondroitin-6-sulfates, chondroitin-4-sulfates, keratins, keratin sulfates, dermatins, dermatan sulfates, dextrans, plasma expanders, including polygeline ("Haemaccel", degraded gelatin polypeptide cross-linked via urea bridges, produced by "Behring"), "hydroxyethylstarch" (Hetastarch, HES) and extrans, food and drug additives, soluble cellulose derivatives (e.g., methylcellulose, carboxymethylcellulose), polyaminoacids, hydrocarbon polymers (e.g., polyethylene), polystyrenes, polyesters, polyamides, polyethylene oxides (e.g. polyethyleneglycols, polycarboxyethyleneglycols, polycarboxylated polyethyleneglycols), polyvinnylpyrrolidones, polysaccharides, polypyranoses, alginates, assimilable gums (e.g., xanthan gum), peptides, injectable blood proteins (e.g., serum albumin), cyclodextrin, and derivatives thereof.

In one embodiment, polysaccharides may be homo-polysaccharides, while in another embodiment, they may be hetero-polysaccharides.

In one embodiment, examples of monomers, dimers, and oligomers which can be employed as the conjugated moiety for producing Lipid-conjugates for use in the methods of the invention may be mono- or disaccharides, trisaccharides, oligopeptides, carboxylic acids, dicarboxylic acids, fatty acids, dicarboxylic fatty acids, salicylates, slicyclic acids, acetyl salicylic acids, aspirins, lactobionic acids, maltoses, amino acids, glycines, glutaric acids, succinic acids, dodecanoic acids, didodecanoic acids, bile acids, cholic acids, cholesterylhemisuccinates, and di- and trisaccharide unit monomers of polysaccharides, polypyranoses, and/or glycosaminoglycans including heparins, heparan sulfates, hyaluronic acids, chondroitins, chondroitin sulfates, chondroitin-6-sulfates, chondroitin-4-sulfates, dermatitis, dermatan sulfates, keratins, keratan sulfates, or dextrans.

In some cases, according to embodiments of the invention, the monomer or polymer chosen for preparation of the Lipid-conjugate may in itself have select biological properties. For example, both heparin and hyaluronic acid are materials with known physiological functions. In the present invention, however, the Lipid-conjugates formed from these substances as starting materials display a new and wider set of pharmaceutical activities than would be predicted from administration of either heparin or hyaluronic acid which have not been bound by covalent linkage to a phospholipid. It can be shown, by standard comparative experiments as described below and in U.S. application Ser. No. 10/952,496, incorporated herein by reference, that phosphatidylethanolamine (PE) linked to hyaluronic acid (Compound XXII), to heparin (Compound XXIV), to chondroitin sulfate A (Compound XXV), to carboxymethylcellulose (Compound XXVI), to Polygeline (haemaccel) (Compound XXVII), or to hydroxyethylstarch (Compound XXVIII), are far superior in terms of potency and range of useful pharmaceutical activity to the free conjugates (the polymers above and the like). In fact, these latter substances are, in general, not considered useful in methods for treatment of conjunctivitis. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone.

The biologically active Lipid-conjugates described herein can have a wide range of molecular weights, e.g., above 50,000 (up to a few hundred thousands) when it is to desirable to retain the Lipid conjugate in the vascular system and below 50,000 when targeting to extravascular systems is desirable. The sole limitation on the molecular weight and the chemical structure of the conjugated moiety is that it does not result in a Lipid-conjugate devoid of the desired biological activity, or lead to chemical or physiological instability to the extent that the Lipid-conjugate is rendered useless as a drug in the method of use described herein.

In one embodiment, the compound for use in the present invention is represented by the structure of the general formula (A):

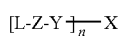
(A)

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a physiologically acceptable monomer, dimer, oligomer, or polymer; and
n is a number from 1 to 1000;
wherein any bond between L, Z, Y and X is either an amide or an esteric bond.

In one embodiment, L is phosphatidyl, Z is ethanolamine, wherein L and Z are chemically bonded resulting in phosphatidylethanolamine, Y is nothing, and X is carboxymethylcellulose. In another embodiment, L is phosphatidyl, Z is ethanolamine, wherein L and Z are chemically bonded resulting in phosphatidylethanolamine, Y is nothing, and X is a glycosaminoglycan. In one embodiment, the phosphatidylethanolamine moiety is dipalmitoyl phosphatidylethanolamine. In another embodiment, the phosphatidylethanolamine moiety is dimyristoyl phosphatidylethanolamine.

In another embodiment, the compound for use in the present invention is represented by the structure of the general formula (I):

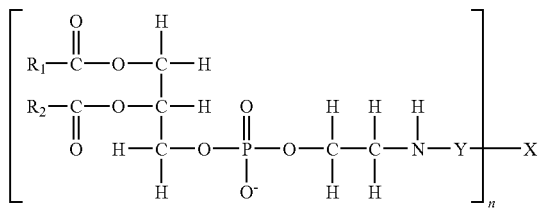
(I)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms; and
X is either a physiologically acceptable monomer, dimer, oligomer or a physiologically acceptable polymer; and
n is a number from 1 to 1,000;
wherein if Y is nothing the phosphatidylethanolamine is directly linked to X via an amide bond and if Y is a spacer, the spacer is directly linked to X via an amide or an esteric bond and to the phosphatidylethanolamine via an amide bond.

In one embodiment, compounds for use in the methods of the invention comprise one of the following as the conjugated moiety X: acetate, butyrate, glutarate, succinate, dodecanoate, didodecanoate, maltose, lactobionic acid, dextran, alginate, aspirin, cholate, cholesterylhemisuccinate, carboxymethyl-cellulose, heparin, hyaluronic acid, chondroitin sulfate, polygeline (haemaccel), polyethyleneglycol, polycarboxylated polyethylene glycol, a glycosaminoglycan, a polysaccharide, a hetero-polysaccharide, a homo-polysaccharide, or a polypyranose. The polymers used as starting material to prepare the PE-conjugates may vary in molecular weight from 1 to 2,000 kDa.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. In one embodiment, the PE moiety is dipalmitoyl-phosphatidyl-ethanolamine. In another embodiment, the PE moiety is dimyristoyl-phosphatidyl-ethanolamine.

Phosphatidyl-ethanolamine and its analogues may be from various sources, including natural, synthetic, and semisynthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylserine (PS) and its analogues, such as palmitoyl-stearoyl-PS, natural PS from various sources, semisynthetic PSs, synthetic, natural and artifactual PSs and their isomers. Other phospholipids useful as conjugated moieties in this invention are phosphatidylcholine (PC), phosphatidylinositol (PI), phosphatidic acid and phosphoatidylglycerol (PG), as well as derivatives thereof comprising either phospholipids, lysophospholipids, phosphatidic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In another embodiment, the compound for use in the present invention is represented by the structure of the general formula (II):

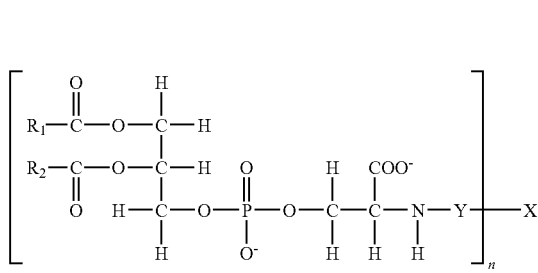

(II)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Y is either nothing or a spacer group ranging in length from 2 to 30 atoms;
- X is a physiologically acceptable monomer, dimer, oligomer or polymer wherein
- X is a glycosaminoglycan; and
- n is a number from 1 to 1000;
- wherein if Y is nothing, the phosphatidylserine is directly linked to X via an amide bond and if Y is a spacer, the spacer is directly linked to X via an amide or an esteric bond and to the phosphatidylserine via an amide bond.

In one embodiment, the phosphatidylserine may be bonded to Y, or to X if Y is nothing, via the COO⁻ moiety of the phosphatidylserine.

In another embodiment, the compound for use in the present invention is represented by the structure of the general formula (III):

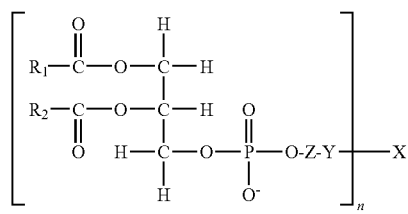

(III)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, inositol, choline, or glycerol;
- Y is either nothing or a spacer group ranging in length from 2 to 30 atoms;
- X is a physiologically acceptable monomer, dimer, oligomer, or polymer wherein
- X is a glycosaminoglycan; and
- n is a number from 1 to 1000;
- wherein any bond between the phosphatidyl, Z, Y and X is either an amide or an esteric bond.

In another embodiment, the compound for use in the present invention is represented by the structure of the general formula (IV):

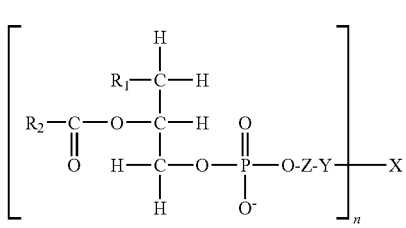

(IV)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, inositol, choline, or glycerol;
- Y is either nothing or a spacer group ranging in length from 2 to 30 atoms;
- X is a physiologically acceptable monomer, dimer, oligomer, or polymer wherein
- X is a glycosaminoglycan; and
- n is a number from 1 to 1000;
- wherein any bond between the phospholipid, Z, Y and X is either an amide or an esteric bond.

In another embodiment, the compound for use in the present invention is represented by the structure of the general formula (V):

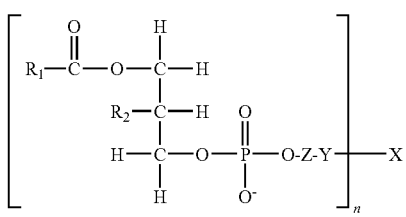

(V)

wherein
- $R_1$ is a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, inositol, choline, or glycerol;
- Y is either nothing or a spacer group ranging in length from 2 to 30 atoms;
- X is a physiologically acceptable monomer, dimer, oligomer, or polymer wherein
- X is a glycosaminoglycan; and
- n is a number from 1 to 1000;
- wherein any bond between the phospholipid, Z, Y and X is either an amide or an esteric bond.

In another embodiment, the compound for use in the present invention is represented by the structure of the general formula (VI):

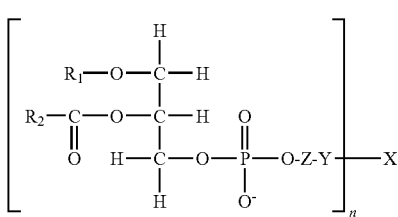

(VI)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, inositol, choline, or glycerol;
- Y is either nothing or a spacer group ranging in length from 2 to 30 atoms;
- X is a physiologically acceptable monomer, dimer, oligomer, or polymer wherein
- X is a glycosaminoglycan; and
- n is a number from 1 to 1000;
- wherein any bond between the phospholipid, Z, Y and X is either an amide or an esteric bond.

In another embodiment, the compound for use in the present invention is represented by the structure of the general formula (VII):

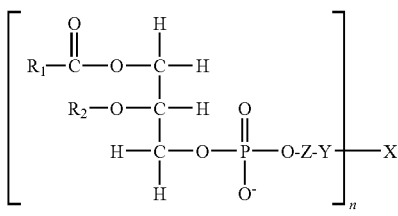

(VII)

wherein
- $R_1$ is a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, inositol, choline, or glycerol;
- Y is either nothing or a spacer group ranging in length from 2 to 30 atoms;
- X is a physiologically acceptable monomer, dimer, oligomer, or polymer wherein
- X is a glycosaminoglycan; and
- n is a number from 1 to 1000;
- wherein any bond between the phospholipid, Z, Y and X is either an amide or an esteric bond.

In one embodiment of the invention, phosphatidylcholine (PC), phosphatidylinositol (PI), phosphatidic acid (PA), wherein Z is nothing, and phosphatidylglycerol (PG) conjugates are herein defined as compounds of the general formula (III).

In another embodiment, the compound for use in the present invention is represented by the structure of the general formula (VIII):

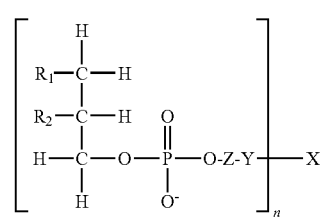

(VIII)

wherein
- $R_1$ is a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein
- X is a glycosaminoglycan; and
- n is a number from 1 to 1000;
- wherein any bond between the phospholipid, Z, Y and X is either an amide or an esteric bond.

In another embodiment, the compound for use in the present invention is represented by the structure of the general formula (IX):

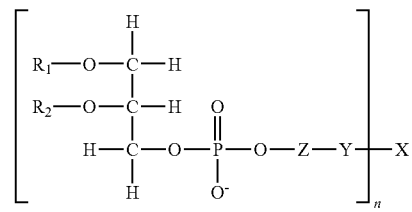

(IX)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein
- X is a glycosaminoglycan; and
- n is a number from 1 to 1000;
- wherein any bond between the phospholipid, Z, Y and X is either an amide or an esteric bond.

In another embodiment, the compound for use in the present invention is represented by the structure of the general formula (IXa):

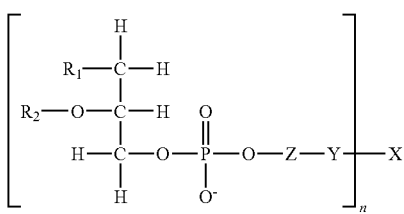
(IXa)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein
- X is a glycosaminoglycan; and
- n is a number from 1 to 1000;
- wherein any bond between the phospholipid, Z, Y and X is either an amide or an esteric bond.

In another embodiment, the compound for use in the present invention is represented by the structure of the general formula (IXb):

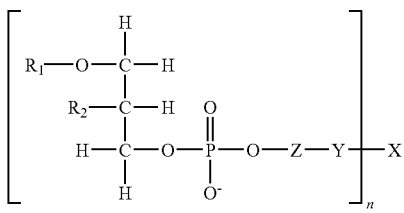
(IXb)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein
- X is a glycosaminoglycan; and
- n is a number from 1 to 1000;
- wherein any bond between the phospholipid, Z, Y and X is either an amide or an esteric bond.

In another embodiment, the compound for use in the present invention is represented by the structure of the general formula (X):

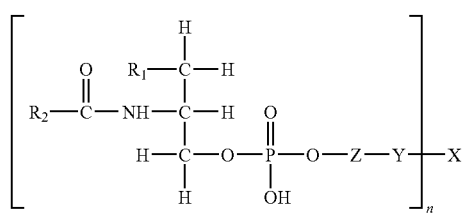
(X)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein
- X is a glycosaminoglycan; and
- n is a number from 1 to 1000;
- wherein any bond between the ceramide phosphoryl, Z, Y and X is either an amide or an esteric bond.

In another embodiment, the compound for use in the present invention is represented by the structure of the general formula (XI):

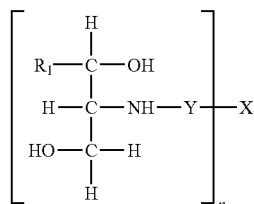
(XI)

wherein
- $R_1$ is a linear, saturated, mono-unsaturated, or poly-unsaturated, alkyl chain ranging in length from 2 to 30 carbon atoms;
- Y is either nothing or a spacer group ranging in length from 2 to 30 atoms;
- X is a physiologically acceptable monomer, dimer, oligomer or polymer wherein
- X is a glycosaminoglycan; and
- n is a number from 1 to 1000;
- wherein if Y is nothing the sphingosyl is directly linked to X via an amide bond and if Y is a spacer, the spacer is directly linked to X and to the sphingosyl via an amide bond and to X via an amide or an esteric bond.

In another embodiment, the compound for use in the present invention is represented by the structure of the general formula (XII):

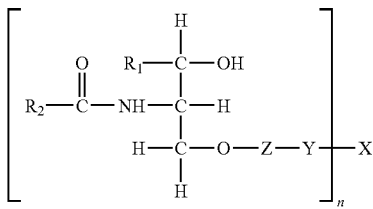

(XII)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer or polymer wherein
- X is a glycosaminoglycan; and
- n is a number from 1 to 1000;
- wherein any bond between the ceramide, Z, Y and X is either an amide or an esteric bond.

In another embodiment, the compound for use in the present invention is represented by the structure of the general formula (XIII):

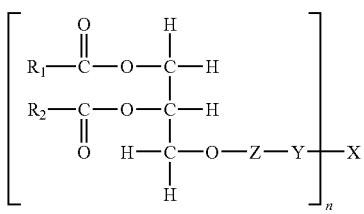

(XIII)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein
- X is a glycosaminoglycan; and
- n is a number from 1 to 1000;
- wherein any bond between the diglyceryl, Z, Y and X is either an amide or an esteric bond.

In another embodiment, the compound for use in the present invention is represented by the structure of the general formula (XIV):

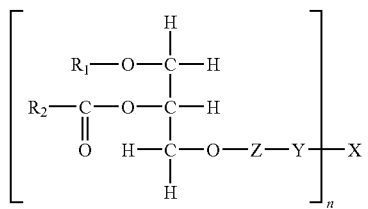

(XIV)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein
- X is a glycosaminoglycan; and
- n is a number from 1 to 1000;
- wherein any bond between the glycerolipid, Z, Y and X is either an amide or an esteric bond.

In another embodiment, the compound for use in the present invention is represented by the structure of the general formula (XV):

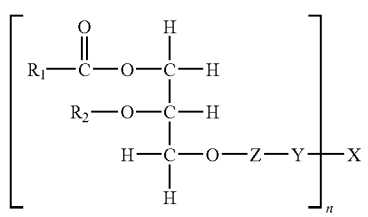

(XV)

wherein
- $R_1$ is a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein
- X is a glycosaminoglycan; and
- n is a number from 1 to 1000;
- wherein any bond between the glycerolipid, Z, Y and X is either an amide or an esteric bond.

In another embodiment, the compound for use in the present invention is represented by the structure of the general formula (XVI):

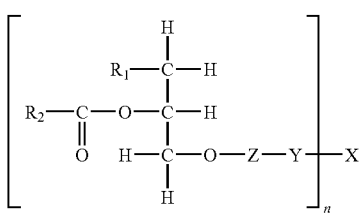

(XVI)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein
- X is a glycosaminoglycan; and
- n is a number from 1 to 1000;
- wherein any bond between the lipid, Z, Y and X is either an amide or an esteric bond.

In another embodiment, the compound for use in the present invention is represented by the structure of the general formula (XVII):

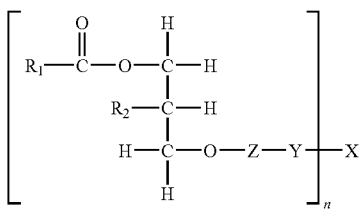

(XVII)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein
- X is a glycosaminoglycan; and
- n is a number from 1 to 1000;
- wherein any bond between the lipid, Z, Y and X is either an amide or an esteric bond.

In another embodiment, the compound for use in the present invention is represented by the structure of the general formula (XVIII):

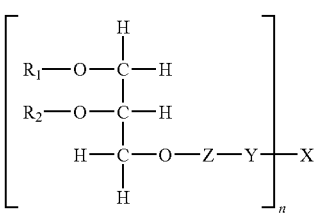

(XVIII)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein
- X is a glycosaminoglycan; and
- n is a number from 1 to 1000;
- wherein any bond between the lipid, Z, Y and X is either an amide or an esteric bond.

In another embodiment, the compound for use in the present invention is represented by the structure of the general formula (XIX):

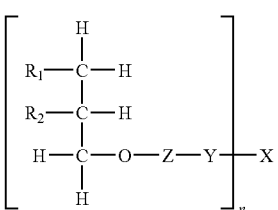

(XIX)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein
- X is a glycosaminoglycan; and
- n is a number from 1 to 1000;
- wherein any bond between the lipid, Z, Y and X is either an amide or an esteric bond.

In another embodiment, the compound for use in the present invention is represented by the structure of the general formula (XX):

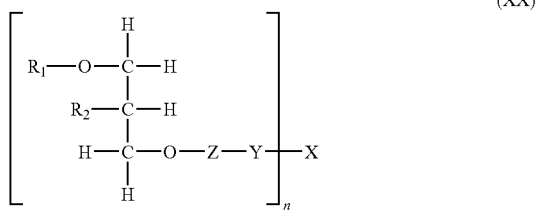

(XX)

wherein
R₁ is either hydrogen or a linear, saturated, mono-unsaturated, or poly-unsaturated, alkyl chain ranging in length from 2 to 30 carbon atoms;
R₂ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer wherein
X is a glycosaminoglycan; and
n is a number from 1 to 1000;
wherein any bond between the lipid, Z, Y and X is either an amide or an esteric bond.

In another embodiment, the compound for use in the present invention is represented by the structure of the general formula (XXI):

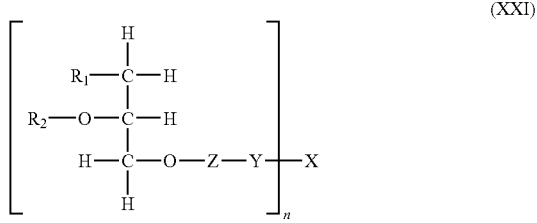

(XXI)

wherein
R₁ is either hydrogen or a linear, saturated, mono-unsaturated, or poly-unsaturated, alkyl chain ranging in length from 2 to 30 carbon atoms;
R₂ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a physiologically acceptable monomer, dimer, oligomer or polymer wherein
X is a glycosaminoglycan; and
n is a number from 1 to 1000;
wherein any bond between the lipid, Z, Y and X is either an amide or an esteric bond.

For any or all of the compounds represented by the structures of the general formulae (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), and (XXII) hereinabove: In one embodiment, X is a glycosaminoglycan. According to this aspect and in one embodiment, the glycosaminoglycan may be, inter alia, hyaluronic acid, heparin, heparan sulfate, chondroitin sulfate, keratin, keratan sulfate, dermatan sulfate or a derivative thereof. In another embodiment, X is not a glycosaminoglycan. In another embodiment, X is a polysaccharide, which in one embodiment is a hetero-polysaccharide, and in another embodiment, is a homo-polysaccharide. In another embodiment, X is a polypyranose.

In another embodiment, the glycosaminoglycan is a polymer of disaccharide units. In another embodiment, the number of the disaccharide units in the polymer is m. In another embodiment, m is a number from 2-10,000. In another embodiment, m is a number from 2-500. In another embodiment, m is a number from 2-1000. In another embodiment, m is a number from 50-500. In another embodiment, m is a number from 2-2000. In another embodiment, m is a number from 500-2000. In another embodiment, m is a number from 1000-2000. In another embodiment, m is a number from 2000-5000. In another embodiment, m is a number from 3000-7000. In another embodiment, m is a number from 5000-10,000. In another embodiment, a disaccharide unit of a glycosaminoglycan may be bound to one lipid or phospholipid moiety. In another embodiment, each disaccharide unit of the glycosaminoglycan may be bound to zero or one lipid or phospholipid moieties. In another embodiment, the lipid or phospholipid moieties are bound to the —COOH group of the disaccharide unit. In another embodiment, the bond between the lipid or phospholipid moiety and the disaccharide unit is an amide bond.

In another embodiment, the chondroitin sulfate may be, inter alia, chondroitin-6-sulfate, chondroitin-4-sulfate or a derivative thereof.

In one embodiment of the invention, Y is nothing. Non-limiting examples of suitable divalent groups forming the optional bridging group (which in one embodiment, is referred to as a spacer) Y, according to embodiments of the invention, are straight or branched chain alkylene, e.g., of 2 or more, preferably 4 to 30 carbon atoms, —CO-alkylene-CO, —NH-alkylene-NH—, —CO-alkylene-NH—, —NH-alkylene-NH, CO-alkylene-NH—, an amino acid, cycloalkylene, wherein alkylene in each instance, is straight or branched chain and contains 2 or more, preferably 2 to 30 atoms in the chain, —(—O—CH(CH₃)CH₂—)ₓ— wherein x is an integer of 1 or more.

According to embodiments of the invention, in addition to the traditional phospholipid structure, related derivatives for use in this invention are phospholipids modified at the C1 or C2 position to contain an amine, ether or alkyl bond instead of an ester bond. In one embodiment of the invention, the alkyl phospholipid derivatives and ether phospholipid derivatives are exemplified herein.

In one embodiment of the invention, the sugar rings of the glycosaminoglycan are intact. In another embodiment, intact refers to closed. In another embodiment, intact refers to natural. In another embodiment, intact refers to unbroken.

In one embodiment of the invention, the structure of the lipid or phospholipid in any compound according to the invention is intact. In another embodiment, the natural structure of the lipid or phospholipids in any compound according to the invention is maintained.

In one embodiment, the compounds for use in the present invention are biodegradable.

In one embodiment, the compound according to the invention is phosphatidylethanolamine bound to aspirin. In one embodiment, the compound according to the invention is phosphatidylethanolamine bound to glutarate.

In some embodiments, the compounds for use are as listed in Table 1 below.

TABLE 1

| Phospholipid | Spacer | Polymer (m.w.) | Compound |
|---|---|---|---|
| PE | None | Hyaluronic acid (2-2000 kDa) | XXII |
| Dimyristoyl-PE | None | Hyaluronic acid | XXIII |
| PE | None | Heparin (0.5-110 kDa) | XXIV |
| PE | None | Chondroitin sulfate A | XXV |
| PE | None | Carboxymethylcellulose (20-500 kDa) | XXVI |
| PE | Dicarboxylic acid + Diamine | Polygeline (haemaccel) (4-40 kDa) | XXVII |
| PE | None | Hydroxyethylstarch | XXVIII |
| PE | Dicarboxylic acid + Diamine | Dextran (1-2,000 kDa) | XXIX |
| PE | None | Aspirin | XXX |
| PE | Carboxyl amino group | Hyaluronic acid (2-2000 kDa) | XXXI |
| PE | Dicarboxyl group | Hyaluronic acid (2-2000 kDa) | XXXII |
| PE | Dipalmitoic acid | Hyaluronic acid (2-2000 kDa) | XXXIII |
| PE | Carboxyl amino group | Heparin (0.5-110 kDa) | XXXIV |
| PE | Dicarboxyl group | Heparin (0.5-110 kDa) | XXXV |
| PE | Carboxyl amino group | Chondroitin sulfate A | XXXVI |
| PE | Dicarboxyl group | Chondroitin sulfate A | XXXVII |
| PE | Carboxyl amino group | Carboxymethylcellulose (20-500 kDa) | XXXVIII |
| PE | Dicarboxyl group | Carboxymethylcellulose (20-500 kDa) | XXXIX |
| PE | None | Polygeline (haemaccel) (4-40 kDa) | XL |
| PE | Carboxyl amino group | Polygeline (haemaccel) (4-40 kDa) | XLI |
| PE | Dicarboxyl group | Polygeline (haemaccel) (4-40 kDa) | XLII |
| PE | Carboxyl amino group | Hydroxyethylstarch | XLIII |
| PE | Dicarboxyl group | Hydroxyethylstarch | XLIV |
| PE | None | Dextran (1-2,000 kDa) | XLV |
| PE | Carboxyl amino group | Dextran (1-2,000 kDa) | XLVI |
| PE | Dicarboxyl group | Dextran (1-2,000 kDa) | XLVII |
| PE | Carboxyl amino group | Aspirin | XLVIII |
| PE | Dicarboxyl group | Aspirin | XLIX |
| PE | None | Albumin | L |
| PE | None | Alginate (2-2000 kDa) | LI |
| PE | None | Polyaminoacid | LII |
| PE | None | Polyethylene glycol | LIII |
| PE | None | Lactobionic acid | LIV |
| PE | None | Acetylsalicylate | LV |
| PE | None | Cholesteryl- hemmisuccinate | LVI |
| PE | None | Maltose | LVII |
| PE | None | Cholic acid | LVIII |
| PE | None | Chondroitin sulfates | LIX |
| PE | None | Polycarboxylated polyethylene glycol | LX |
| Dipalmitoyl-PE | None | Hyaluronic acid | LXI |
| Dipalmitoyl-PE | None | Heparin | LXII |
| Dipalmitoyl-PE | None | Chondroitin sulfate A | LXIII |
| Dipalmitoyl-PE | None | Carboxymethylcellulose | LXIV |
| Dipalmitoyl-PE | None | Polygeline (haemaccel) | LXV |
| Dipalmitoyl-PE | None | Hydroxyethylstarch | LXVI |
| Dipalmitoyl-PE | None | Dextran | LXVII |
| Dipalmitoyl-PE | None | Aspirin | LXVIII |
| Dimyristoyl-PE | None | Heparin | LXVIX |
| Dimyristoyl-PE | None | Chondroitin sulfate A | LXX |
| Dimyristoyl-PE | None | Carboxymethylcellulose | LXXI |
| Dimyristoyl-PE | None | Polygeline (haemaccel) | LXXII |
| Dimyristoyl-PE | None | Hydroxyethylstarch | LXXIII |
| Dimyristoyl-PE | None | Dextran | LXXIV |
| Dimyristoyl-PE | None | Aspirin | LXXV |
| PS | None | Hyaluronic acid | LXXVI |
| PS | None | Heparin | LXXVII |
| PS | None | Polygeline (haemaccel) | LXXVIII |
| PC | None | Hyaluronic acid | LXXIX |
| PC | None | Heparin | LXXX |
| PC | None | Polygeline (haemaccel) | LXXXI |
| PI | None | Hyaluronic acid | LXXXII |
| PI | None | Heparin | LXXXIII |
| PI | None | Polygeline (haemaccel) | LXXXIV |
| PG | None | Hyaluronic acid | LXXXV |
| PG | None | Heparin | LXXXVI |
| PG | None | Polygeline (haemaccel) | LXXXVII |
| PE | None | Glutaryl | LXXXVIII |

In one embodiment of the invention, the compounds for use in the present invention are any one or more of Compounds I-LXXXVIII. In another embodiment, the compounds for use in the present invention are Compound XXII, Compound XXIII, Compound XXIV, Compound XXV, Compound XXVI, Compound XXVII, Compound XXVIII, Compound XXIX, Compound XXX, or pharmaceutically acceptable salts thereof, in combination with a physiologically acceptable carrier or solvent. According to embodiments of the invention, these polymers, when chosen as the conjugated moiety, may vary in molecular weights from 200 to 2,000,000 Daltons. In one embodiment of the invention, the molecular weight of the polymer as referred to herein is from 200 to 1000 Daltons. In another embodiment, the molecular weight of the polymer as referred to herein is from 200 to 1000 Daltons. In another embodiment, the molecular weight of the polymer as referred to herein is from 1000 to 5000 Daltons. In another embodiment, the molecular weight of the polymer as referred to herein is from 5000 to 10,000 Daltons. In another embodiment, the molecular weight of the polymer as referred to herein is from 10,000 to 20,000 Daltons. In another embodiment, the molecular weight of the polymer as referred to herein is from 10,000 to 50,000 Daltons. In another embodiment, the molecular weight of the polymer as referred to herein is from 20,000 to 70,000 Daltons. In another embodiment, the molecular weight of the polymer as referred to herein is from 50,000 to 100,000 Daltons. In another embodiment, the molecular weight of the polymer as referred to herein is from 100,000 to 200,000 Daltons. In another embodiment, the molecular weight of the polymer as referred to herein is from 200,000 to 500,000 Daltons. In another embodiment, the molecular weight of the polymer as referred to herein is from 200,000 to 1,000,000 Daltons. In another embodiment, the molecular weight of the polymer as referred to herein is from 500,000 to 1,000,000 Daltons. In another embodiment, the molecular weight of the polymer as referred to herein is from 1,000,000 to 2,000,000 Daltons. Various molecular weight species have been shown to have the desired biological efficacy.

In one embodiment of this invention, low molecular weight Lipid-conjugates are defined hereinabove as the compounds of formula (I)-(XXI) wherein X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid, glycosaminoglycan, or polypyranose.

Examples of suitable divalent groups forming the optional bridging group Y are straight- or branched chain alkylene, e.g., of 2 or more, preferably 4 to 18 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 18 carbon atoms in the chain, —(—O—CH(CH$_3$)CH$_2$—)$_x$— wherein x is an integer of 1 or more.

In another embodiment, in addition to the traditional phospholipid structure, related derivatives for use in this invention are phospholipids modified at the C1 or C2 position to contain an ether or alkyl bond instead of an ester bond. These derivatives are exemplified hereinabove by the general formulae (VIII) and (IX).

In one embodiment of the invention, X is covalently conjugated to a lipid. In another embodiment, X is covalently conjugated to a lipid via an amide bond. In another embodiment, X is covalently conjugated to a lipid via an esteric bond. In another embodiment, the lipid is phosphatidylethanolamine.

In one embodiment, cell surface GAGs play a key role in protecting cells from diverse damaging agents and processes, such as reactive oxygen species and free radicals, endotoxins, cytokines, invasion promoting enzymes, and agents that induce and/or facilitate degradation of extracellular matrix and basal membrane, cell invasiveness, white cell extravasation and infiltration, chemotaxis, and others. In addition, cell surface GAGs protect cells from bacterial, viral and parasitic infection, and their stripping exposes the cell to interaction and subsequent internalization of the microorganism. Enrichment of cell surface GAGs would thus assist in protection of the cell from injurious processes. Thus, in one embodiment of the invention, PLA2 inhibitors are conjugated to GAGs or GAG-mimicking molecules. In another embodiment, these Lipid-conjugates provide wide-range protection from diverse injurious processes, and are effective in amelioration of diseases that requires cell protection from injurious biochemical mediators.

In another embodiment, a GAG-mimicking molecule may be, inter alia, a negatively charged molecule. In another embodiment, a GAG-mimicking molecule may be, inter alia, a salicylate derivative. In another embodiment, a GAG-mimicking molecule may be, inter alia, a dicarboxylic acid.

In another embodiment, the invention provides a pharmaceutical composition for treating a subject suffering from conjunctivitis, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from conjunctivitis, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII), or any combination thereof.

Preparation of Compounds for Use in the Present Invention

In one embodiment, the preparation of high molecular weight Lipid-conjugates for use in the methods of the present invention is as described in U.S. Pat. No. 5,064,817, which is incorporated fully herein by reference. In one embodiment, these synthetic methods are applicable to the preparation of low molecular weight Lipid-conjugates as well, i.e. Lipid-conjugates comprising monomers and dimers as the conjugated moiety, with appropriate modifications in the procedure as would be readily evident to one skilled in the art. The preparation of some low molecular weight Lipid-conjugates may be conducted using methods well known in the art or as described in U.S. patent application Ser. No. 10/952,496, which is incorporated herein by reference in its entirety.

Without further elaboration, it is believed that one skilled in the art can, using the preceding description, utilize the present invention to its fullest extent. The following preferred specific embodiments are, therefore, to be construed as merely illustrative, and not limiting the remainder of the disclosure in any way whatsoever.

EXAMPLES

The abbreviations used in the examples below are:
PE=phosphatidyl-ethanolamine
HA=hyaluronic acid
Cpd=Compound
Compound XXII=dipalmitoyl-PE conjugated to HA
Compound XXIII=dimyristoyl-phosphatidyl-ethanolamine linked to HA
Compound XXIV=PE conjugated to heparin
Compound XXV=PE conjugated to chondroitin sulfate A (CSA)
Compound XXVI=PE conjugated to carboxymethyl cellulose (CMC)
Compound XXVII=PE conjugated to Polygeline (haemaccel)
Cpd XXIX=PE conjugated to dextran
Cpd XXX=PE conjugated to aspirin
Cpd LXXXVIII=PE conjugated to glutaryl
The compounds used in the examples below were prepared as described in U.S. patent application Ser. No. 10/952,496, which is fully incorporated herein by reference.

Example 1

Treatment of Conjunctivitis

The Lipid-conjugates are effective in the treatment of animal models of conjunctivitis.

Guinea pigs were sensitized with two I.P. injections of 10 mg ovalbumin dissolved in 0.5 ml PBS supplemented with Freunds adjuvant given one week apart. Three weeks after the initial sensitization injection, the first challenge was performed by intraocular dripping of 5 mg ovalbumin dissolved in 25 ml PBS, and repeated challenges were performed 2, 4, 8, and 15 days after the first challenge (FIGS. 1 and 2). On days 2, 4, 8, and 15 days after the first challenge, ovalbumin solution was dripped into the right eye of each animal concurrently with saline (control), carboxymethylcellulose, Compound XXVI, or steroid suspended in PBS. Corneal opacity was evaluated immediately after (FIG. 1) and several hours after (FIG. 2) each challenge.

Ophthalmic levels of the inflammatory modulators LTB4 and $PGE_2$ were determined by ELISA (FIG. 3). For comparison, the effect of steroid treatment was evaluated in parallel. Lipid-conjugates readily improved conjunctivitis in these animals.

Example 2

Viral Infection

Conjunctivitis may be a result of local or systemic viral infection.

In order to demonstrate that the Lipid-conjugates are capable of preventing HIV infection of target cells, whole blood units were mixed with HIV and a Lipid-conjugate (50 μM Compound XXIV, 30 μM Compound XXII) for 30 min. The cells were then spun and the supernatant was examined for HIV infectivity on HT4-1022 cells as described by Margolis-Nunn et al. (Transfusion, 36, 743-750, 1996). FIG. 4 demonstrates the ability of Lipid-conjugates to prevent HIV infection of cells.

Tables 2.1-2.2 demonstrate the capacity of the Lipid-conjugates to inhibit HIV replication, as expressed by the production of the nucleocapsid p24 antigen, which is produced in the host cell upon its infection by HIV virus. [31]MT-2 cells ($10^4$) in 96-well plates were infected with a dose of HIV-1 sufficient to accomplish a multiplicity of infection of 0.0045 in 200 μl of RPMI 1640 medium supplemented with 10% (v/v) fetal bovine serum (FBS), in the absence (control) and presence of the indicated Lipid-conjugate. After 1 h, half of the culture medium was changed and replaced by fresh medium (with/without Lipid-conjugate) and after 24 h, the second half of the culture medium was changed and replaced by fresh medium (with/without Lipid-conjugate). On the fourth day after incubation at 37° C., 100 μl of culture supernatants were collected from each well and an equal volume of fresh medium was added to the wells. The collected supernatants were mixed with an equal volume of 5% (v/v) Triton X-100 and assayed for p24 antigen using an ELISA kit from Coulter Immunology (Hialeah, Fla.).

TABLE 2.1

Inhibition of p24 production

| Compound | $IC_{50}$ (mean ± SD) μg/ml | $IC_{90}$ (mean ± SD) μg/ml |
|---|---|---|
| Compound XXII | 207.0 ± 18.0 | 384.3 ± 79.3 |
| Compound XXIII | 118.0 ± 16.8 | 296.3 ± 104.0 |
| Compound XXIV | 10.0 ± 2.3 | 19.3 ± 4.5 |
| Compound XXV | 72.5 ± 8.0 | 106.0 ± 10.3 |
| Compound XXVII | 375.8 ± 119.5 | >500 |

TABLE 2.2

Inhibition of p24 production

| Compound | $IC_{50}$ (μM) | $IC_{90}$ (μM) |
|---|---|---|
| Compound XXIII | 1.77 | 4.44 |
| Compound XXII | 3.11 | 5.76 |
| Compound XXIV | 0.70 | 1.35 |
| Compound XXV | 1.45 | 2.12 |

Lipid-conjugates inhibited fusion between HIV-1-infected and HIV-uninfected cells. In this assay, HIV-1$_{IIIB}$-infected H9 cells were labeled with BCECF (2',7'-bis(2-carboxyethyl)-5-6-carboxyfluorescein-acetoxymethyl-ester, Molecular Probes, Eugene, Oreg.) according to the manufacturer's instructions. BCECF-labeled H9/HIV-1 IIIB cells ($10^4$) were mixed with $1 \times 10^5$ uninfected MT-2 cells. After incubation in a 96-well plate at 37° C. for 2 h, the fused and unfused labeled cells were counted under an inverted fluorescence microscope at ×160 magnification. At least 200 BCECF-labeled cells were counted and the proportion of fused cells was determined. Fusion tests were carried out in the presence and absence of graded quantities of the tested Lipid-conjugates. Data are presented as the $IC_{50}$ and $IC_{90}$ of the lipid conjugates tested (Table 2.3). The $IC_{50}$ represents the concentration of a drug that is required to achieve 50% inhibition. Similarly, the $IC_{90}$ represents the concentration of a drug that is required to achieve 90% inhibition.

TABLE 2.3

Inhibition of fusion between HIV-infected and uninfected cells.

| Compound | $IC_{50}$ (mean ± SD) μg/ml | $IC_{90}$ (mean ± SD) μg/ml |
| --- | --- | --- |
| Compound XXII | >500 | >500 |
| Compound XXIII | 122.8 ± 14.8 | 219.8 ± 10.6 |
| Compound XXIV | 7.9 ± 1.3 | 15.3 ± 3.9 |
| Compound XXV | >500 | >500 |
| Compound XXVII | >500 | >500 |

In another experiment, whole blood units were mixed with HIV and Lipid-conjugates (between 30 μM and 50 μM) for 30 min. Cells were spun, and supernatant was examined for HIV infectivity on HT4-1022 cells (Table 2.4).

TABLE 2.4

Inhibition of fusion between HIV-infected and uninfected cells.

| Compound | $IC_{50}$ (μM) | $IC_{90}$ (μM) |
| --- | --- | --- |
| Compound XXII | >7.5 | >7.5 |
| Compound XXIII | 1.83 | 3.30 |
| Compound XXIV | 0.55 | 1.07 |
| Compound XXV | >10 | >10 |

Table 2.5 also demonstrates the ability of Lipid-conjugates to inhibit HIV infection. V3 antibody binding is an assay that uses an antibody that binds to the V3 (third variable) domain of the human immunodeficiency virus type 1 (HIV-1) envelope glycoprotein gp120. Anti-V3 domain antibodies may provide an indicator of the presence and amount of HIV. V3 antibody binding was determined by standard ELISA.

TABLE 2.5

Effect of Lipid-conjugates on V3 antibody binding

| Compound | $IC_{50}$ (μM) |
| --- | --- |
| Compound XXII | 45 |
| Compound XXIII | 3 |
| Compound XXIV | 140 |
| Compound XXV | 0.2 |

These experiments demonstrate that administration of Lipid-conjugates is an effective therapy in the treatment HIV, including prevention of infection, replication and fusion.

The effect of Lipid-conjugate treatment on human influenza virus infection in vitro was evaluated as well.

Virus and cell lines. Each virus was obtained from the source described in Table 2.6. Kidney cell lines were obtained from American Type Culture Collection (ATCC). The cells were grown in minimal essential medium (Gibco-BRL, Gaithersburg, Md.) supplemented with 0.1% $NaHCO_3$ and 5 to 9% fetal bovine serum (HyClone Laboratories, Logan, Utah). When performing antiviral assays, serum was reduced to 2% and 50 μg gentamicin (Sigma Chemical Company, St. Louis, Mo.) per ml was added to the medium

TABLE 2.6

Description of viruses used in a screen of some Lipid-conjugates

| Virus | Strain | Source | Cell line |
| --- | --- | --- | --- |
| Influenza type A | A/New Caledonia/ 20/99 (H1N1) | Center for Disease Control and Prevention [CDC] | Madin Darby canine kidney (MDCK) cells |
| | A/Panama/ 2007/99 (H3N2) | CDC | Madin Darby canine kidney (MDCK) cells |
| Influenza type B | B/Hong Kong/330/02 | CDC | Madin Darby canine kidney (MDCK) cells |
| Pichinde virus | An 4763 | Dr. J. D. Gangemi, Univ. of South Carolina School of Medicine, Columbia, SC | African green monkey kidney (BS-C-1) cells |
| Punta Toro virus | Adames | U.S. Army Medical Research Institute for Infectious Diseases, Fort Derrick, Frederick, MD | Rhesus monkey kidney (LLC-MK2) cells |
| Respiratory syncytial virus | A2 | ATCC | African green monkey kidney (MA-104) cells |

1. Inhibition of Viral Cytopathic Effect (CPE)
   A. Visual Observation
   A viral CPE assay was performed as described (Barnard D L et al. Antivir Chem. Chemother. 2001 July; 12(4):241-250).

Compounds were evaluated using four log 10 dilutions of each test compound (e.g., 1000, 100, 10, 1 µg/ml) (Tables 2.7 and 2.8) with an additional concentration of 2000 µg/ml for some experiments (Tables 2.9 and 2.10). Viruses (Influenza type A Strain H1N1, Influenza type A Strain H3N2, Influenza type B, Pichinde virus, Punta Toro virus, and Respiratory syncytial virus) were used at a multiplicity of infection (MOI) of 0.001 to 0.010. The MOIs used were virus dependent and chosen for each strain such that 100% of the cells in the virus controls showed cytopathic effects (CPE) within 5 to 7 days. Cell were grown to an 18 h monolayer (80-100% confluent) in 96-well tissue culture plates and were incubated with various concentrations of each compound as described above. Within 5 minutes of compound incubation, a volume of virus equal to that of the compound was added to the cells. The plates were then sealed and incubated at 37° C. for approximately 72 to 120 hr until the cells in the virus control wells showed complete viral CPE as observed by light microscopy.

Each concentration of drug was assayed for virus inhibition in triplicate. Three wells were set aside as uninfected, untreated cell controls per test and three wells per test compound receive untreated, virus-infected cells and represented positive controls for virus replication. Ribavirin, used as a positive control drug, was evaluated in parallel with compounds for each virus.

The 50% effective concentrations ($EC_{50}$) were calculated by regression analysis of the means of the CPE ratings as compared to untreated, uninfected controls for each concentration. Cells were rated based on changes in enlargement, granularity, ragged edges, filmy appearance, rounding, detachment from the surface of the well, and other changes. Morphological changes results from cytotoxicity of a compound were graded on a scale of 0-5; 0=no toxicity, 1=partial toxicity-slight, 2=partial toxicity, 3=partial toxicity-heavy, 4=partial toxicity-very heavy, and 5=complete cytotoxicity, based on the degree of cytotoxicity observed. The CPE results were then quantified spectrophotometrically by neutral red (NR) uptake assay (see below).

B. Increase in Neutral Red (NR) Dye Uptake
   A Neutral Red Dye Uptake assay was performed as described previously (McManus, N H, Appl. Environment. Microbiol. 31:35-38, 1976) to verify the inhibitory activity and cytotoxicity that was observed in the CPE inhibition assay. Briefly, medium was removed from each well of a plate scored for CPE from a CPE inhibition assay, 0.034% NR in Sörenson's citrate buffer (pH 4.0) was added to each well of the plate and the plate incubated for 2 h at 37° C. in the dark. The NR solution was removed from the wells. After rinsing and aspirating to dryness, the remaining dye was extracted for 30 min, at room temperature in the dark, from the cells using absolute ethanol buffered with Sörenson's citrate buffer. The percentage of NR uptake, indicating viable cells, was read on a microplate autoreader (Bio-Tek EL 1309; Bio-Tek Instruments, Winooski, Vt., USA) at dual wavelengths of 405 and 540 nm. The difference between the two readings were calculated to eliminate background. Absorbance values were expressed as percentages of untreated controls, and EC50 values were calculated as described above.

2. Cytotoxicity Assay
   A. Visual Observation
   Uninfected cells were treated with each concentration of test compound in duplicate and run in parallel with the infected, treated wells in the CPE inhibition tests described above. The toxicity control cells (uninfected and treated) were examined under a light microscope for changes in cell appearance compared to control cells (uninfected, untreated) on the same plate as described above. The 50% cell inhibitory (cytotoxic) concentrations ($IC_{50}$) were calculated by regression analysis.

B. Neutral Red Uptake
   The toxicity control cells (uninfected and treated) described in the previous section were further examined for neutral red dye uptake compared to control cells (uninfected, untreated) on the same plate. Neutral red was added to the toxicity control wells, and the degree of color intensity was determined spectrophotometrically as described above. A neutral red IC50 (NR IC50) was subsequently determined. Absorbance values were expressed as percentages of uninfected, untreated controls, and $IC_{50}$ values were calculated as described above.

3. Data Analysis
   Each test compound's antiviral activity was expressed as a selectivity index (SI), which is the $IC_{50}$ divided by the $EC_{50}$. Generally, an SI of 10 or greater is indicative of positive antiviral activity, although other factors, such as a low SI for the positive control, are also taken into consideration.

Tables 2.7 and 2.8 demonstrate the capacity of the Lipid-conjugates evaluated at low concentration to prevent infection of target cells by influenza virus.

Nine compounds were evaluated for in vitro antiviral testing against influenza A (H1N1 strain) virus, influenza A (H3N2 strain) virus, influenza B virus, respiratory syncitial virus (RSV), Punta Toro virus, and Pichinde virus using various kidney cell lines described in Table 2.6. Two series of Lipid-conjugate dosages were used as described in the methods hereinabove.

Using a lower range of doses, Compound XXIV had significant anti-viral activity against influenza A (H1N1 strain) virus (Table 2.7). The EC50 vs this virus was 5 µg/ml by visual assay and 2.5 µg/ml by neutral red assay, with an IC50 (cytotoxicity)>100 µg/ml. Against the influenza A (H3N2 strain) virus, the EC50 was 35 µg/ml by visual assay and 45 µg/ml by neutral red assay with the same IC50 as above. Compound XXIV was also efficacious vs RSV, with an EC50 of 4 µg/ml using visual assay only, but was not active by neutral red assay. Compound XXIV did not display a virus inhibitory effect against Punta Toro virus at the concentrations tested.

Compound XXV was less active, with EC50 values vs the influenza A (H1N1 strain) virus of 50 µg/ml by visual assay and 35 µg/ml by neutral red assay and an IC50>100 µg/ml (Table 2.8). This compound did not demonstrate a virus inhibitory effect against influenza A (H3N2 strain), influenza B, or RSV at the concentrations tested. Compound XXV did not display a virus inhibitory effect against Punta Toro virus.

TABLE 2.7

Antiviral activity of Compound XXIV (dipalmitoyl-phosphatidyl-ethanolamine conjugated to heparin) at low concentrations

| Virus | $EC_{50}$ (µg/ml) | SI ($IC_{50}/EC_{50}$) |
|---|---|---|
| Visual Observation Assay | | |
| Punta Toro A | >100 | 0 |
| Respiratory Syncytial A | 4 | 25 |
| Influenza A (H1N1 strain) | 5 | 20 |
| Influenza A (H3N2 strain) | 35 | 2.9 |
| Neutral Red Uptake Assay | | |
| Punta Toro A | >100 | 0 |
| Respiratory Syncytial A | >100 | 0 |

TABLE 2.7-continued

Antiviral activity of Compound XXIV (dipalmitoyl-phosphatidyl-ethanolamine conjugated to heparin) at low concentrations

| Virus | $EC_{50}$ (µg/ml) | SI ($IC_{50}/EC_{50}$) |
|---|---|---|
| Influenza A (H1N1 strain) | 2.5 | 40 |
| Influenza A (H3N2 strain) | 45 | 2.2 |

SI—selectivity index. Generally, an SI ≧ 10 is indicative of positive antiviral activity, although other factors such as a low SI for the positive control are also taken into consideration. $IC_{50}$ for Compound XXIV was >100 µg/ml for all viruses.

TABLE 2.8

Antiviral activity of Compound XXV (dipalmitoyl-phosphatidyl-ethanolamine (PE) conjugated to chondroitin-sulfate A) at low concentrations

| Virus | $EC_{50}$ (µg/ml) | SI ($IC_{50}/EC_{50}$) |
|---|---|---|
| Visual Observation Assay | | |
| Punta Toro A | >100 | 0 |
| Influenza A (H1N1 strain) | 50 | 2 |
| Neutral Red Uptake Assay | | |
| Punta Toro A | >100 | 0 |
| Influenza A (H1N1 strain) | 35 | 2.9 |

SI—selectivity index. $IC_{50}$ for Compound XXV was >100 µg/ml for all viruses.

Using higher concentrations of Lipid-conjugates, the results demonstrate a strong effect of Compound XXIV (100) against infection with Influenza A virus H1N1 strain (Tables 2.9 and 2.10). In addition, Compound XXIII (170) and Compound XXIII (80) showed antiviral activity against the H3N2 strain of Influenza A virus in the visual test but not the neutral red assay (Table 2.10).

TABLE 2.9

Antiviral activity of Compound XXIV (dipalmitoyl-phosphatidyl-ethanolamine conjugated to heparin; MK-610) at high concentration

| Virus | $IC_{50}$ (µg/ml) | $EC_{50}$ (µg/ml) | SI ($IC_{50}/EC_{50}$) |
|---|---|---|---|
| Visual Observation Assay | | | |
| Influenza A (H1N1 strain) | 35 | 400 | 11 |
| Influenza A (H3N2 strain) | 100 | 200 | 2 |
| Influenza B | 90 | 350 | 3.9 |
| Neutral Red Uptake Assay | | | |
| Influenza A (H1N1 strain) | 64 | 1000 | 15.6 |
| Influenza A (H3N2 strain) | 110 | 900 | 8.2 |
| Influenza B | 220 | 450 | 2 |

TABLE 2.10

Antiviral activity of Lipid-Conjugates against Influenza A (H1N1 and H3N2 strains) and Influenza B viruses at high concentration.

| Compound (phosphate content) Name | Influenza A (H1N1 strain) Visual | NR | Influenza A (H3N2 strain) Visual | NR | Influenza B Visual | NR |
|---|---|---|---|---|---|---|
| Ribavirin | 22 | 25 | 56 | 36 | 22 | 19 |
| Compound XXIV (100) | 11 | 15.6 | 2 | 8.2 | 3.9 | 2 |
| Compound XXII (170) | 3.6 | 0 | 25 | 0 | 10 | 0 |
| Compound XXV (60) | 2.5 | 0 | 0 | 0 | 0 | 0 |
| Compound XXIII (80) | 0 | 0 | 10 | 6.5 | 0 | 0 |
| Compound XXV (230) | 0 | 0 | 6.7 | 7.2 | 0 | 0 |
| Compound XXII (85) | 0 | 0 | 2.5 | 0 | 0 | 0 |
| Compound XXIV (50) | 0 | 0 | 0 | 0 | 0 | 0 |
| Compound XXII (40) | 0 | 0 | 0 | 0 | 0 | 0 |
| Compound XXV (100) | 0 | 0 | 0 | 0 | 0 | 0 |

SI—selectivity index ($IC_{50}/EC_{50}$);
Visual = Visual Observation Assay;
NR = Neutral Red Uptake Assay The effect of Lipid-conjugate treatment on human influenza virus infection in vivo was assessed, as well. Young adult (18-21 g) female BALB/c mice were infected intranasally with either influenza A/NWS/33 (H1N1), A/PR8/34 (H1N1), A/New Caledonia/20/99 (H1N1), A/Victoria/3/75 (H3N2), A/Port Chalmers/1/73 (H3N2), B/Hong Kong/5/72, B/Lee/40, B/Sichuan/379/99, or A/Duck/MN/1525/81 (H5N1) virus at sufficient dose to render death in approximately 90% of the mice, with the mean day to death being 6-10 days. The animals are monitored for arterial oxygen saturation levels using a pulse oximeter on days 3 through 11 (the infection usually induces major declines in these levels by about day 9-10 due to lung consolidation). We also sacrifice mice on days 1, 3, 6, and 9 for assay of lung score, lung weight increase, and lung virus titer. We usually use 22 infected mice for each dosage of test compound, and 35 infected mice treated with placebo. Three uninfected mice are included as toxicity controls, these are treated in parallel to the above, and weight loss or gain is determined during the period of treatment. A group of normal controls are also run in parallel to ascertain their weight gain during the study as well as the normal arterial oxygen saturation levels. Some of these animals are also killed to determine normal lung parameters.

If the test compound is considered to be an immunomodulator, we would inject mice with the compound intraperitoneally every other day for a total of 4 treatments beginning 24 h prior to virus exposure. If the material is considered to be antiviral, a twice daily for 5 days treatment schedule is recommended, with therapy beginning 4 h pre-virus exposure. We generally try to select three dosages varying 2-fold or ½ log 10 from each other, with the high dose being approximately the maximum tolerated dose.

Ribavirin is usually included at a single dose as a known positive control.

The effect of Lipid-conjugate treatment on vaccinia virus infection in vitro was evaluated, as well.

BS-C-1 cell monolayers ($3 \times 10^6$ cells), in 3 cm diameter plastic dishes, were infected with a dilution of a crude stock of vaccinia virus (WR strain), to give a m.o.i. of 1 PFU per 10 cells. After adsorption for 1 hr, the cells were washed and 2 ml of Dulbecco's MEM, supplemented with 2% fetal calf serum, containing 1:10 dilution of the compound to be tested, were added. The cultures were incubated for 2 days at 37° C. and then harvested. Control infected cultures that were not treated with the compounds, were harvested at 0 time and at 48 hr. The virus titer in all cultures was determined, after three cycles of freezing and thawing, by plaque assay in BS-C-1 cells.

Table 2.11 demonstrates the capacity of the Lipid-conjugates to prevent infection of target cells by vaccinia virus. Compounds XXII, XXIII, and XXV inhibited viral infection in culture by 62-99%.

TABLE 2.11

Antiviral activity of Lipid-Conjugates against Vaccinia virus

| Time (PFU/culture) (hr) | Compound tested | Virus titer | % inhibition |
|---|---|---|---|
| 0 | — | less than $10^4$ | |
| 48 | — | $8.6 \times 10^7$ | 0% |
| 48 | Compound XXII-40* | $3.3 \times 10^6$ | 96.2% |
| 48 | Compound XXII-80* | $2.3 \times 10^7$ | 73.3% |
| 48 | Compound XXIII | $7.7 \times 10^4$ | 99.9% |
| 48 | Compound XXV | $3.2 \times 10^7$ | 62.8% |

*The number expresses the amount of nmoles lipid conjugated to 1 mg of polymer.

The administration of phospholipid polypyranose conjugates was thus exemplified herein in treating viral infection, a common cause of conjunctivitis.

Example 3

Treatment of *Chlamydia* Infection

Bacterial infection is another common cause of conjunctivitis, in particular, infection with chalmydial species.

The ability of Lipid-conjugate treatment to prevent infection of HeLa cells by *Chlamydia* was thus evaluated. The human cervical adenocarcinoma cell line, HeLa 229 (ATCC, Manassas, Calif.), was cultured and incubated with the phospholipid conjugates (20 micromolar) for 30 min, then incubated with *Chlamydia psittaci* (an avian form of *Chlamydia trachomatis*) (guinea pig inclusion conjunctivitis serologically variant strains (servovars)) for 24 hr. Infected cells were detected by cytofluorometry (FACS) using FITC-conjugated anti-Chlamydia antibody (FIG. 5, top).

FIG. 5 (bottom) depicts the dose response of the Lipid-conjugates' inhibitory effect on infection of HeLa cells by *Chlamydia*. HeLa cells were treated with the Lipid-conjugates at the indicated concentration, and infected with *Chlamydia* as described above.

Lipid-conjugates were shown to inhibit *Chlamydia*-induced cell apoptosis. HeLa cells were treated with Lipid-conjugates and infected with *Chlamydia psittaci* as in Experiment 3. For determination of apoptosis, detergent-permeabilized cells were stained with propidium iodide, and their fluorescence was measured by cytofluorometry (FIG. 6).

Thus phospholipid polypyranose conjugates as exemplified herein, were effective in the prophylaxis and treatment of infection with a bacterial pathogen, which is a known cause of conjunctivitis.

Example 4

Hemolysis

Hemolysis, the breakdown of red blood cells (RBC), may be either a primary disease in itself, or a syndrome associated with another disease or physiological insult. In order to determine the effect of Lipid-conjugates on hemolysis, red blood cells were incubated in the presence of known membrane destabilizing agents and the release of hemoglobulin into the extracellular medium was detected.

Experiment 4.1 demonstrates that the Lipid-conjugates serve to maintain the stability of human red blood cells exposed to membrane-destroying agents. Human RBC were washed in saline and suspended in Hanks buffer (pH 7.4). Hemolysis was induced in the absence or presence of 10 μM Lipid-conjugates by treatment with either 5 U/ml streptolysin O (SLO), 25 U/ml streptolysin S (SLS), or 5 μg/ml lysophosphatidylcholine (lyso-PC) for 20 min. The cell membranes were spun and the hemoglobin content in the supernatant was determined by measuring the O.D. at 540 nm (Table 4.1).

TABLE 4.1

Prevention of Hemolysis by Compound XXII, Compound XXVI and Compound XXIV

| | HEMOLYSIS (O.D. AT 540 nm) | | |
|---|---|---|---|
| Lipid-conjugate | SLO | SLS | Lyso-PC |
| None | 1.000 | 1.000 | 1.000 |
| HA | 1.000 | 1.000 | 1.875 |
| Compound XXII-30* | 0.650 | 0.750 | 0.335 |
| Compound XXII-60* | 0.012 | 0.005 | 0.017 |
| Compound XXII-110* | 0.005 | 0.002 | 0.012 |
| Compound XXIV | 0.002 | 1.100 | 0.002 |
| Compound XXVI-60* | 0.012 | 0.005 | 0.002 |
| Compound XXVI-110* | 0.002 | | 0.002 |

*The number expresses the amount of nmoles lipid conjugated to 1 mg of polymer.

These experiments demonstrate that the Lipid-conjugates are effective therapy in the treatment of cell membrane rupture and/or hemolysis. Thus, Lipid-conjugates protect against membrane destabilization, which may be a mechanism through which they are useful for the methods of the present invention. For example, Lipid-conjugates may protect against cytopathic effects due to infection or cell to cell spread of pathogens that cause conjunctivitis.

Example 5

Anti-Oxidant Therapy

The noxious effect of peroxide free radicals on living tissue is known as oxidative damage. When cell membranes are the targets for this damaging process, membrane dysfunction and instability result. Oxidative damage to blood proteins, particularly blood lipid proteins, results in their over-accumulation in cells lining the vasculature, thus contributing to atherogenesis. In fact, oxidative cell damage is a major mechanism attributed to the process of aging or senescence.

In order to determine the effect of Lipid-conjugates on oxidative damage to proteins or cell membranes, tissue was exposed to hydrogen peroxide ($H_2O_2$) produced by (a) the enzyme glucose oxidase (GO) in the absence or presence of additional membrane destabilizing agents such as $PLA_2$ or (b) by exposure to divalent cations, such as copper.

Experiments 5.1-5.3 demonstrate the ability of Lipid-conjugates to preserve cells from oxidative damage, as judged by the cells' retention of both arachidonic acid and of low molecular weight intracellular substances.

Experiment 5.1: Confluent BGM (green monkey kidney epithelial) cells were labeled with $^3$H-arachidonic acid. The cells were treated with Compound XXVI for 30 min prior to treatment with GO and $PLA_2$ (0.5 U/ml) (FIG. 7).

Experiment 5.2: BGM cells were labeled with $^{35}SO_4$ overnight. The cells were washed with DMEM (containing 10 mg/ml BSA) 4 times with PBS. The cells were then incubated in DMEM supplemented with GO (an $H_2O_2$ generator) for 90 min, and the culture medium was collected and counted for $^{35}$S radioactivity. For treatment with Compound XXVI, cells were incubated with 3 or 10 μM Compound XXVI for 30 min prior to introduction of GO. Data are presented as mean±SEM for 5 replications. *p<0.005; **p<0.001 (FIG. 8).

Experiment 5.3 demonstrates the ability of Lipid-conjugates to inhibit the oxidation of blood lipoprotein. Low density lipoprotein (LDL; 0.1 µM) and or hydroperoxides (LOON) were incubated in the absence and presence of various concentrations of Compound XXII or HA at 37° C. At time zero, 5 µM $CuCl_2$ was added to the dispersions, and the mixtures were continuously monitored for oxidation products at 245 nm (FIG. 9). The absorbance at 245 (OD units) is depicted as a function of time (Schnitzer et al., Free Radical Biol Med 24; 1294-1303, 1998).

These experiments demonstrate that administration of Lipid-conjugates is an effective therapy to prevent tissue damage induced by oxidative stress (associated with free radical and hydrogen peroxide production) by a plurality of mechanisms, including inhibiting the oxidation of lipoprotein, inhibiting arachidonic acid release, and preserving the integrity of cell membranes (inhibiting GAG degradation), including red blood cell membranes, as described above. The efficacy of Lipid-conjugates in protecting against tissue damage induced by oxidative stress may contribute to their usefulness in treating conjunctivitis.

Example 6

Skin Diseases, Contact Dermatitis and Psoriasis

Contact dermatitis is a widespread skin disease and is often attributed to a delayed type hypersensitivity response. Cutaneous, or skin, hypersensitivity reactions may occur in response to virtually any material and may present clinically in either acute or chronic form. A widely-accepted system for invoking the delayed type hypersensitivity response is systemic sensitization to an antigen followed by its local application. Psoriasis is another common form of dermatitis marked by plaque-like formations, evident on extensor surfaces. As a hyperproliferative disorder of epithelial cells, drug therapies are typically examined in cell cultures obtained from sufferers of the condition.

Both secreted (sPLA) and cytosolic (cPLA) PLA2 have been identified in human skin. Their inflammatory roles have been determined in patients suffering from inflammatory skin diseases such as psoriasis, although some also play a role in maintaining healthy skin integrity.

Experiments 6.1-6.4 demonstrate that treatment of animals afflicted with a hypersensitivity reaction readily respond to the administration of Lipid-conjugates, whether applied intraperitoneally (Table 6.1), subcutaneously (Table 6.2), or topically (Tables 6.3-6.4), as both prophylactic and acute therapy.

Four modes of administration were performed: 1) The Lipid-conjugate in saline was injected intraperitoneally daily beginning day 0 until day 6 (Table 6.1); 2) The Lipid-conjugate in saline was injected subcutaneously into the ear (adjacent to the challenged area) in two injections, either 3 h before application of oxalozone to the ear or 1 h after application of oxalozone to the ear (Table 6.2); 3) $EtOH:H_2O$ 1:1 was applied topically to both ears on top of the challenged area daily beginning day 0 until day 6 (Table 6.3); 4) the Lipid-conjugate was applied topically only to the right ear for 5 times 4-6 hours following the challenge (Table 6.4) using either 20 µL of 0.1% Compound XXIX in 50% EtOH or 20 µl of Dermovat (steroid ointment). In all experiments control Group A (late sensitized only) was treated by topical application of oxalozone to both sides of the ear 24 hours before measuring its swelling. Group B (fully sensitized+saline or EtOH 50% was treated by topical application of oxalozone to the shaved stomach and then on day 6 by topical application of oxalozone to both sides of the ear. Swelling was measured in 0.1 to mm by subtracting normal ear width of each individual mouse from the width after treatment. Percent inhibition was calculated by the net swelling of the Lipid-conjugate-treated ear (over that of the control group A), divided by the net swelling of the fully-sensitized ear. As shown in Tables 6.1-6.4, in all cases, treatment with the Lipid-conjugates clearly reduced ear swelling in DTH-induced mice. Of particular interest are the results presented in Table 6.4, showing that although the topical administration of the drug was unilateral in both cases, the steroid affected both ears, while the topically applied Lipid-conjugate affected only the area to which it was applied, indicative of a lack of systemic infiltration of the Lipid-conjugate in this context.

TABLE 6.1

Attenuation of Dermal DTH Response by Compound XXVI - Intraperitoneal Administration

| Group | Treatment | No. of Mice | Swelling after sensitization − Swelling of normal ear (0.1 mm) Mean ± S.D. (n = 12) | Percent inhibition |
|---|---|---|---|---|
| A | Control (late sensitized) | 6 | 1.8 ± 1.0 | — |
| B | Fully sensitized + saline | 6 | 18.5 ± 0.97 | — |
| C | Fully sensitized + CMC 40 mg (0.4 µmol/kg) | 6 | 19.8 ± 1.13 | — |
| D | Fully sensitized + Cpd XXVI 40 mg (0.4 µmol/kg) | 6 | 7.9 ± 1.37 | 66 |
| E | Fully sensitized + betamethasone 5 mg (15 µmol/kg) | 6 | 6.5 ± 1.35 | 74 |

TABLE 6.2

Attenuation of Dermal DTH Response by Compound XXVI - Subcutaneous Administration

| Group | Treatment | No. of Mice | Swelling after sensitization − Swelling of normal ear (0.1 mm) Mean + S.D. (n = 12) | Percent inhibition |
|---|---|---|---|---|
| A | Control (late sensitized) | 5 | 4.1 ± 0.82 | — |
| B | Fully sensitized + saline | 5 | 18.3 ± 0.82 | — |

TABLE 6.2-continued

Attenuation of Dermal DTH Response by Compound XXVI - Subcutaneous Administration

| Group | Treatment | No. of Mice | Swelling after sensitization – Swelling of normal ear (0.1 mm) Mean + S.D. (n = 12) | Percent inhibition |
|---|---|---|---|---|
| C | Fully sensitized + CMC (carrier polymer only)40 mg (0.4 µmol/kg) | 5 | 13.5 ± 2.17 | 35 |
| D | Fully sensitized + Cpd XXVI 40 mg (0.4 µmol/kg) | 5 | 5.9 ± 1.52 | 87 |
| E | Fully sensitized + betamethasone 1 mg (3 µmol/kg) | 5 | 8.1 ± 1.19 | 72 |

TABLE 6.3

Attenuation of Dermal DTH Response by Compound XXIX - Topical Administration

| Group | Treatment | No. of Mice | Swelling after sensitization – Swelling of normal ear (0.1 mm) Mean + S.D. (n = 12) | Percent Inhibition |
|---|---|---|---|---|
| A | Control (late sensitized only) | 5 | 1.5 ± 0.70 | — |
| B | Fully sensitized + saline | 5 | 24.3 ± 1.56 | — |
| C | Fully sensitized + Dextran (carrer polymer only) (0.5 µmol/kg) | 5 | 24.4 ± 2.4 | — |
| D | Fully sensitized + Compound XXIX (0.5 µmol/kg) | 5 | 12.17 ± 1.52 | 53 |
| E | Fully sensitized + betamethasone (3 µmol/kg) | 5 | 10.6 ± 0.84 | 60 |

TABLE 6.4

Attenuation of Dermal DTH Response by Compound XXIX - Unilateral Topical Administration vs Steroid Preparation

| Group | Treatment | No. of mice | Swelling after sensitization- Swelling of normal ear (0.1 mm) Mean ± S.D. (n = 10) | | | Percent Inhibition | |
|---|---|---|---|---|---|---|---|
| | | | Left ear | Both ears | Right ear | Left ear | Right ear |
| A | Control, (late sensitized only) | 10 | | 1.0 ± 2.0 | | — | — |
| B | Fully sensitized + vehicle (dextran) | 10 | | 23.0 ± 4.0 | | — | — |
| C | Fully sensitized + Compound XXIX (0.5 µmol/kg), on right ear only. | 7 | 20.0 ± 1.0 | | 11.0 ± 1.0 | 14 | 46 |
| D | Fully sensitized + betamethasone (3 µmol/kg, dermovat) on right ear only. | 7 | 7.0 ± 1.0 | | 7.0 ± 1.0 | 63 | 63 |

Experiment 6.5: To show that Lipid-conjugates effectively inhibit the proliferation of cultured psoriatic skin fibroblasts and Swiss 3T3 cells. Fibroblasts of human psoriatic skin (dermis) cells, (full circles) or Swiss 3T3 cells (empty circles) were treated with Compound XXVI at the indicated concentration for three days, after which the cells were counted (FIG. 10). The cell number of the control, untreated group at the end of the three day incubation was taken as 100%. For comparison, carboxymethylcellulose was tested alone (square).

Experiment 6.6: To show that Lipid-conjugates are effective in treating patients with contact dermatitis, a double-blind, placebo-controlled study was conducted in patients with contact dermatitis.
Methods Drug preparation: A topical preparation of 1% HYPE (MW~50 kDa) was prepared by the Hadassah pharmacy (Jerusalem, Israel) using the following w/w % ratios: Water 70.0, Cetyl Alcohol, 10.6, Paraffin, White soft 10.6, Propylene Glycol 7.2, HyPE 1.0 and Sodium Dodecyl Sulfate 0.6.

Study design and experimental procedures: The study group comprised a total of 11 female patients aged 19-50 (mean age: 34.6). All the patients had received a clinical diagnosis of contact dermatitis and a positive patch test to at least a single allergen. The disease distribution was symmetrical in all patients at the study sites. All patients exhibited contact dermatitis on the surface of their hands with some patients exhibiting the disease on their forearms as well. Patients refrained from any systemic treatment for no less than a month before the intitation of the study and from topical treatment for no less than two weeks before the study. Disease severity was evaluated before treatment (day 0) and after a month of treatment (day 30) by the physician assessment scoring criteria (ranging from 0 to 3) described in Table 6.5. In the initial analysis, the scores for each criteria were assigned and summed to give a total score for each patient, with a minumum possible severity score of 0 and a maximum possible severity score of 15. The range of severity scores for patients in the initial evaluation was 8-15.

TABLE 6.5

Physician assessment scoring criteria for contact dermatitis

| | | |
|---|---|---|
| Dryness | 0-none | 3-very dry |
| Scaling | 0-none | 3-severe scaling |
| Redness (erythema) | 0-none | 3-severe redness |
| Pruritus (itching) | 0-none | 3-very pruritic |
| Fissures | 0-none | 3-deep fissures |

Each patient received two color-coded tubes of cream. One tube contained the active pharmaceutical ingredient (Compound XXII), and the other tube contained just the vehicle (placebo). Except for their label color, the tubes were identical in size, and the tube contents were identical in color and odor. The doctor and the patients were unaware of which tube contained the Compound XXII. Patients were instructed to consistently apply cream twice a day. They were instructed to apply the cream from the blue marked tube to their right hand and forearm and to apply cream from the pink marked tube to their left hand and forearm. The same doctor evaluated the patients before and after treatment. The study was approved by the Helsinki Committee of Israeli Ministry of Health based on animal safety data presented.

Results

All 11 enrolled patients completed the one month study. The mean total score before treatment was 11.27±0.71. After one month of unilateral treatment with the lipid conjugate, marked differences were visible between the right and left hands and arms of the patients. On the Compound XXII-treated side, the average visual score was reduced by 69.9%, while on the placebo-treated side, the average visual score was reduced by 32.9% (p<0.005) (FIG. 11).

These experiments demonstrate that Lipid-conjugates are effective remedies for the management of various forms of dermatitis including skin hypersensitivity reactions and psoriasis. Chronic ocular itch that often results from conjunctivitis often leads to chronic eyelid rubbing and dermatitis.

Example 7

PLA$_2$ Inhibition

The PLA$_2$ enzymes catalyze the hydrolysis of fatty acids attached to phospholipids on the plasma membrane. Arachidonic acid, the main metabolite released from these reactions, is a precursor for other enzymatic reactions mediated by lipoxygenases and cyclooxygenases. These reactions produce prostaglandins and leukotrienes, which have a profound effect on inflammation in vivo. Therefore, PLA$_2$ inhibitors are capable of inhibiting inflammation via their ability to inhibit the production of downstream inflammatory factors.

Experiments were designed to determine the effect of Compound XXII, Compound XXV, Compound XXX, and Compound LXXXVIII on the inhibition of the Naja Naja Snake Venom PLA$_2$ enzyme in an in vitro fluorometric assay. The reaction of the PLA$_2$ enzyme and the PLA$_2$ enzyme substrate 2-(6-(7-nitrobenz-2-oxa-1,3 diazol-4-yl)amino) hexanoyl-1-hexadecanoyl-sn-glycero-3-phosphocholine (NHGP) yields a product, which can be detected using a fluorometer. Decreased absorbance indicates inhibition of the PLA$_2$ enzyme.

Methods

Compound XXII and Compound XXV were solubilized and diluted in D-PBS, and tested at final concentrations of 0.625, 0.125, 0.25, 0.5 and 1 mg/ml. Compound XXX and Compound LXXXVIII were solubilized in 100% dimethyl sulfoxide (DMSO), diluted in D-PBS and tested at final concentrations of 0.01, 0.1 and 1 mg/ml. 1 mM NHGP was diluted in D-PBS, for a final concentration of 1 μM. The positive control, Mefenamic Acid (Sigma, M-4267), was tested at a final concentration of 0.1 mg/ml. The PLA$_2$ enzyme is derived from the Naja Naja Snake Venom (Sigma, P6139) and tested at a final concentration of 5 Units/ml. The reaction was carried out in 200 μl solution and initiated by addition of substrate. Fluorescence was read immediately and then every minute for 30 minutes for a total of 30 readings. The fluorometer was set as follows: Excitation 450/50; Emission 530/25; Gain 50.

Results

Compound XXII inhibited the PLA$_2$ enzyme by 37%, 42%, 71% and 98% at 0.125, 0.25, 0.5 and 1 mg/ml respectively (FIG. 12) compared to 41% inhibition by 0.1 mg/ml mefenamic acid, which served as a positive control. Compound XXV inhibited the PLA$_2$ enzyme, although with no apparent dose response, by 20%, 30% and 26% at 0.625, 0.125, 0.25 mg/ml (FIG. 13). The inhibition of the PLA$_2$ enzyme by Compound LXXXVIII and Compound XXX could not be determined in this assay, due to difficulties in solubilizing the compounds in DMSO, even after sonication.

Thus, Compound XXII inhibits the PLA$_2$ enzyme in a dose-dependent manner, indicating its ability to act as an anti-inflammatory drug. Other experiments showing anti-inflammatory effects of Lipid-conjugates are demonstrated in U.S. application Ser. No. 10/952,496 filed Sep. 29, 2004 and are hereby incorporated by reference.

It will be appreciated by persons skilled in the art that the present invention is not limited by what has been particularly shown and described herein above and that numerous modifications, all of which fall within the scope of the present invention, exist. Rather, the scope of the invention is defined by the claims which follow:

What I claim is:

1. A method of suppressing or inhibiting conjunctivitis in a subject comprising the step of contacting said subject with a compound represented by the structure of the general formula (I) or (II), and/or a pharmaceutical salt or a pharmaceutical composition thereof:

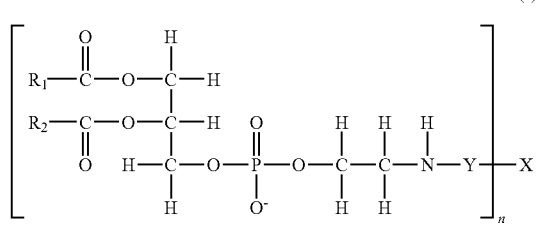

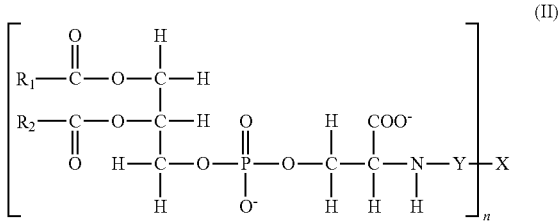 (II)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Y is either nothing or a spacer group ranging in length from 2 to 30 atoms;
- X is a physiologically acceptable monomer, dimer, oligomer or polymer; and
- n is a number from 1 to 1000;
- wherein if Y is nothing, the phospholipid moiety is directly linked to X via an amide bond and if Y is a spacer, the spacer is directly linked to X via an amide or an esteric bond and to the phospholipid moiety via an amide bond.

2. The method according to claim 1, wherein said conjunctivitis is viral conjunctivitis.

3. The method according to claim 1, wherein said conjunctivitis is bacterial conjunctivitis.

4. The method according to claim 1, wherein said conjunctivitis is due to an allergen.

5. The method according to claim 1, wherein said conjunctivitis is due to an irritant.

6. The method according to claim 1, wherein said phospholipid moiety is phosphatidylethanolamine.

7. The method according to claim 6, wherein said phosphatidylethanolamine is dipalmitoyl phosphatidylethanolamine.

8. The method according to claim 6, wherein said phosphatidylethanolamine is dimyristoyl phosphatidylethanolamine.

9. The method according to claim 1, wherein said physiologically acceptable monomer, dimer, oligomer, or polymer is carboxymethylcellulose.

10. The method according to claim 1, wherein $R_1$ and/or $R_2$ are palmitic acid moieties.

11. The method according to claim 1, wherein $R_1$ and/or $R_2$ are myristic acid moieties.

12. The method according to claim 1, wherein X is hyaluronic acid.

13. The method according to claim 1, wherein X is heparin.

14. The method according to claim 1, wherein X is chondroitin sulfate.

15. The method according to claim 1, wherein X is a glycosaminoglycan.

16. The method according to claim 1, wherein X is selected from the group of molecules consisting of polygeline, hydroxyethylstarch, dextran, aspirin, albumin, alginate, polyaminoacid, polyethylene glycol, lactobionic acid, acetylsalicylate, cholesteryl-hemmisuccinate, maltose, cholic acid, polycarboxylated polyethylene glycol, and glutaryl.

17. The method according to claim 1, wherein said phospholipid moiety is phosphatidylserine.

18. The method according to claim 17, wherein said phosphatidylserine is dipalmitoyl phosphatidylserine.

19. The method according to claim 17, wherein said phosphatidylserine is dimyristoyl phosphatidylserine.

20. The method according to claim 1, wherein n is a number from 2 to 1000.

* * * * *